United States Patent
Kennedy

(10) Patent No.: US 6,743,602 B1
(45) Date of Patent: Jun. 1, 2004

(54) POLYNUCLEOTIDES DIFFERENTIALLY EXPRESSED IN ADENOCARCINOMAS, POLYPEPTIDES ENCODED THEREBY, AND METHODS OF USE THEREOF

(75) Inventor: Giulia C. Kennedy, San Francisco, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 09/626,301

(22) Filed: Jul. 25, 2000

Related U.S. Application Data

(60) Provisional application No. 60/148,936, filed on Aug. 13, 1999, and provisional application No. 60/145,612, filed on Jul. 26, 1999.

(51) Int. Cl.⁷ .................................. C12P 21/06
(52) U.S. Cl. ................ 435/69.1; 435/91.1; 435/94; 435/252.3; 435/326; 530/350; 536/23.1; 536/24.3; 536/24.31
(58) Field of Search ................ 536/23.1, 24.3, 536/24.31; 530/350; 435/326, 252.3, 69.1, 91.1, 94

(56) References Cited

U.S. PATENT DOCUMENTS 4,889,806 A * 12/1989 Olson et al. ............. 435/172.3

FOREIGN PATENT DOCUMENTS

| WO | WO 99 57144 | 11/1999 |
| WO | WO 00 58473 | 10/2000 |

OTHER PUBLICATIONS

Putilina, T et al, 1998, Genbank Sequence Database, Accession No: JE0325, and MPSRCH search report, 2002, us–09–626–301–4.rpr, p. 1.*
Nagase et al, 1998, Genbank Sequence Database, Accession No: 015462, and MPSRCH search report, 2002, us–09–626–301–4.rspt, pp. 2–3.*
Taber's cyclopedic medical dictionary, 1989, pp. 1446–1447.*
Putilina, T et al, 1997, Genbank Sequence Database, Accession No: 015452, and MPSRCH search report, 2002, us–09–626–301–2.rspt, pp. 2–3.*
Alberts. Mol. Biol. Cell, 3ʳᵈ ed, p. 465, 1994.*
Shantz. Intl. J. Biochem & Cell Biol, 31:107–122, 1999.*
McClean. Eur. J. Cancer. 29A: 2243–2248, 1993.*
Fu, EMBO J. 15: 4392–4401, 1996.*
Putilina, T. GenBank, Accession No.: U90654 and MPSRCH Search Report p. 5–6, 1997.*
Hillier, GenBank, Accession No: AA100793 and MPSRCH Search Report p. 5–6, 1997.*
Putilina et al. (1998) "Analysis of a human cDNA containing a tissue–specific alternatively spliced LIM domain." *Biochemical and Biophysical Research Communications*, vol. 252(2):433–439.
GenBank, Accession No. AF144237, Jun. 1, 1999.
Carter (1990). "Cancer of the pancreas" *Gut*, vol. 31: 494–496.
Del Villano et al. (1983). "Radioimmunometric assay for a monoclonal antibody–defined tumor marker, CA 19–9" *Clin. Chem.*, vol. 29(3):549–552.
Fabris et al. (1988). "Serum markers and clinical data in diagnosing pancreatic cancer: A contrastive approach" *Am. J. Gastroenterology*, vol. 83(5): 549–553.
Fisher (1975). "The pathology of invasive breast cancer" *Cancer*, vol. 36(1): 1–85.
Frebourg et al. (1988). "The evaluation of CA 19–9 antigen level in the early detection of pancreatic cancer" *Cancer*, vol. 62(11): 2287–2290.
Homma et al. (1991). "The study of the mass screening of person without symptoms and of the screening of outpatients with gastrointestinal complaints or icterus for pancreatic cancer in Japan, using CA 19–9 and Elastase–1 or ultrasonography" *Int. J. Pancreatol.*, vol. 9: 119–124.
Nagase et al. (1998). "Prediction of the coding sequences of unidentified genes. XII. The complete sequencing of 100 new cDNA clones from brain which code for large proteins in vitro" *DNA Res.*, vol. 5: 355–364.
Ritts et al. (1984). "Initial clinical evaluation of an immunoradiometric assay for CA 19–9 using the NCI serum bank" *Int. J. Cancer*, vol. 33: 339–345.
Rhodes et al. (1990). "Serum diagnostic tests for pancreatic cancer" *Baillière's Clinical Gastroenterology*, vol. 4(4): 833–852.
Satake et al. (1990). "A clinical evaluation of various tumor markers for the diagnosis of pancreatic cancer" *Int. J. Pancreatol.*, vol. 7: 25–36.
Satake et al. (1991). "Diagnosis of pancreatic cancer" *Int. J. Pancreatol.*, vol. 9: 93–98.
Steinberg et al. (1990). "The clinical utility of the CA 19–9 tumor–associated antigen" *Am. J. Gastroenterology*, vol. 85(4): 350–355.
GenBank, Accession No. AA005111, May 9, 1997.
GenBank, Accession No. AI079858, Oct. 1, 1998.
GenBank, Accession No. N31885, Jan. 10, 1996.
GenBank, Accession No. AI355866, Feb. 15, 1999.
GenBank, Accession No. AI018075, Aug. 27, 1998.
GenBank, Accession No. AB020665.
GenBank, Accession No. U90654.

* cited by examiner

*Primary Examiner*—Anthony C. Caputa
*Assistant Examiner*—Minh-Tam Davis
(74) *Attorney, Agent, or Firm*—James S. Keddie; Charlene A. Launer; Robert P. Blackburn

(57) ABSTRACT

The present invention features human HX2004-6 polypeptide and nucleotide sequences encoding HX2004-6 polypeptides. In a particular aspect, the polynucleotide is the nucleotide sequence of SEQ ID NO:1. In related aspects the invention features expression vectors and host cells comprising polynucleotides that encode a human HX2004-6 polypeptide. The present invention also relates to antibodies that bind specifically to a human HX2004-6 polypeptide. Further provided are diagnostic and screening methods using HX2004-6 polynucleotides and antibodies specific for HX2004-6 polypeptides.

14 Claims, 11 Drawing Sheets

Figure 2A

ATAGCACGACTGTGTATGCTCTGGAGGACTGAAAGGCTGTACAAGCCCTATGTATTTTTT
TTCAAATATACATATGCATGGGTCTTGCTGCTGCCTCTTTTGCTGACTGTAATTGGACTT
TGAAGCTTCGAAGTTATATCATAAAAATTTGTAACCTTTGTCTGAGAGAGAGCTCAGCTA
AGCAATCACTTTCCACTTCTTTTCACAGGATAATATAAACGTTTTCTTGAAAGCTTGTGA
ACAGATTGGATTGAAAGAAGCCCAGCTTTTCCATCCTGGAGATCTACAGGATTTATCAAA
TCGAGTCACTGTCAAGCAAGAAGAGACTGACAGGAGAGTGAAAATGTTTTGATAACATT
GTACTGGCTGGGAAGAAAAGCACAAAGCAACCCGTACTATAATGGTCCCCATCTTAATTT
GAAAGCGTTTGAGAATCTTTTAGGACAAGCACTGACGAAGGCACTCGAAGACTCCAGCTT
CCTGAAAAGAAGTGGCAGGGACAGTGGCTACGGTGACATCTGGTGTCCTGAACGTGGAGA
ATTTCTTGCTCCTCCAAGGCACCATAAGAGAGAAGATTCCTTTGAAAGCTTGGACTCTTT
GGGCTCGAGGTCATTGACAAGCTGCTCCTCTGATATCACGTTGAGAGGGGGCGTGAAGG
TTTTGAAAGTGACACAGATTCGGAATTTACATTCAAGATGCAGGATTATAATAAAGATGA
TATGTCGTATCGAAGGATTTCGGCTGTTGAGCCAAAGACTGCGTTACCCTTCAATCGTTT
TTTACCCAACAAAAGTAGACAGCCATCCTATGTACCAGCACCTCTGAGAAAGAAAAGCC
AGACAAACATGAGGATAACAGAAGAAGTTGGGCAAGCCCGGTTTATACAGAAGCAGATGG
AACATTTTCAAGGAGTAAGTCCATGAGTGATGTCAGCGCAGAAGATGTTCAAAACTTGCG
TCAGCTGCGTTACGAGGAGATGCAGAAAATAAAATCACAATTAAAAGAACAAGATCAGAA
ATGGCAGGATGACCTTGCAAAATGGAAAGATCGTCGAAAAGTTACACTTCAGATCTGCA
GAAGAAAAAGAAGAGAGAAGAAATTGAAAGCAGGCACTTGAGAAGTCTAAGAGAAG
CTCTAAGACGTTTAAGGAAATGCTGCAGGACAGGGAATCCCAAAATCAAAGTCTACAGT
TCCGTCAAGAAGGAGAATGTATTCTTTTGATGATGTGCTGGAGGAAGGAAAGCGACCCCC
TACAATGACTGTGTCAGAAGCAAGTTACCAGAGTGAGAGAGTAGAAGAGAAGGGAGCAAC
TTATCCTTCAGAAATTCCCAAAGAAGATTCTACCACTTTTGCAAAAAGAGAGGACCGTGT
AACAACTGAAATTCAGCTTCCTTCTCAAAGTCCTGTGGAAGAACAAAGCCCAGCCTCTTT
GTCTTCTCTGCGTTCACGGAGCACACAAATGGAATCAACTCGTGTTTCAGCTTCTCTCCC
CAGAAGTTACCGGAAAACTGATACAGTCAGGTTAACATCTGTGGTCACACCAAGACCCTT
TGGCTCTCAGACAAGGGGAATCTCATCACTCCCCAGATCTTACACGATGGATGATGCTTG
GAAGTATAATGGAGATGTTGAAGACATTAAGAGAACTCCAAACAATGTGGTCAGCACCCC
TGCACCAAGCCCGGACGCAAGCCAACTGGCTTCAAGCTTATCTAGCCAGAAAGAGGTAGC
AGCAACAGAAGAAGATGTGACAAGGCTGCCCTCTCCTACATCCCCCTTCTCATCTCTTTC
CCAAGACCAGGCTGCCACTTCTAAAGCCACATTGTCTTCCACATCTGGTCTTGATTTAAT
GTCTGAATCTGGAGAAGGGGAAATCTCCCCACAAAGAGAAGTCTCAAGATCCCAGGATCA
GTTCAGTGATATGAGAATCAGCATAAACCAGACGCCTGGGAAGAGTCTTGACTTTGGGTT
TACAATAAAATGGGATATTCCTGGGATCTTCGTAGCATCAGTTGAAGCAGGTAGCCCAGC
AGAATTTTCTCAGCTACAAGTAGATGATGAAATTATTGCTATTAACAACACCAAGTTTTC
ATATAACGATTCAAAAGAGTGGGAGGAAGCCATGGCTAAGGCTCAAGAAACTGGACACCT
AGTGATGGATGTGAGGCGCTATGGAAAGGCTGGTTCACCTGAAACAAAGTGGATTGATGC
AACTTCTGGAATTTACAACTCAGAAAAATCTTCAAATCTATCTGTAACAACTGATTTCTC
CGAAAGCCTTCAGAGTTCTAATATTGAATCCAAAGAAATCAATGGAATTCATGATGAAAG
CAATGCTTTTGAATCAAAGCATCTGAATCCATTTCTTTGAAAAACTTAAAAGGCGATC
ACAATTTTTTGAACAAGGAAGCTCTGATTCGGTGGTTCCTGATCTTCCAGTTCCAACCAT
CAGTGCCCCGAGTCGCTGGGTGTGGGATCAAGAGGAGGAGCGGAAGCGGCAGGAGAGGTG
GCAGAAGGAGCAGGACCGCCTACTGCAGGAAAAATATCAACGTGAGCAGGAGAAACTGAG

Figure 2B

GGAAGAGTGGCAAAGGGCCAAACAGGAGGCAGAGAGAGAGAATTCCAAGTACTTGGATGA
GGAACTGATGGTCCTAAGCTCAAACAGCATGTCTCTGACCACACGGGAGCCCTCTCTTGC
CACCTGGGAAGCTACCTGGAGTGAAGGGTCCAAGTCTTCAGACAGAGAAGGAACCCGAGC
AGGAGAAGAGGAGAGGAGACAGCCACAAGAGGAAGTTGTTCATGAGGACCAAGGAAAGAA
GCCGCAGGATCAGCTTGTTATTGAGAGAGAGAGGAAATGGGAGCAACAGCTTCAGGAAGA
GCAAGAGCAAAGCGGCTTCAGGCTGAGGCTGAGGAGCAGAAGCGTCCTGCGGAGGAGCA
GAAGCGCCAGGCAGAGATAGAGCGGGAAACATCAGTCAGAATATACCAGTACAGGAGGCC
TGTTGATTCCTATGATATACCAAAGACAGAAGAAGCATCTTCAGGTTTTCTTCCTGGTGA
CAGGAATAAATCCAGATCTACTACTGAACTGGATGATTACTCCACAAATAAAAATGGAAA
CAATAAATATTTAGACCAAATTGGGAACACGACCTCTTCACAGAGGAGATCCAAGAAAGA
ACAAGTACCATCAGGAGCAGAATTGGAGAGGCAACAAATCCTTCAGGAAATGAGGAAGAG
AACACCCCTTCACAATGACAACAGCTGGATCCGACAGCGCAGTGCCAGTGTCAACAAAGA
GCCTGTTAGTCTTCCTGGGATCATGAGAAGAGGCGAATCTTTAGATAACCTGGACTCCCC
CCGATCCAATTCTTGGAGACAGCCTCCTTGGCTCAATCAGCCCACAGGATTCTATGCTTC
TTCCTCTGTGCAAGACTTTAGTCGCCCACCACCTCAGCTGGTGTCCACATCAAACCGTGC
CTACATGCGGAACCCCTCCTCCAGCGTGCCCCCACCTTCAGCTGGCTCCGTGAAGACCTC
CACCACAGGTGTGGCCACCACACAGTCCCCCACCCCGAGAAGCCATTCCCCTTCAGCTTC
ACAGTCAGGCTCTCAGCTGCGTAACAGGTCAGTCAGTGGGAAGCGCATATGCTCCTACTG
CAATAACATTCTGGGCAAAGGAGCCGCCATGATCATCGAGTCCCTGGGTCTTTGTTATCA
TTTGCATTGTTTTAAGTGTGTTGCCTGTGAGTGTGACCTCGGAGGCTCTTCCTCAGGAGC
TGAAGTCAGGATCAGAAACCACCAACTGTACTGCAACGACTGCTATCTCAGATTCAAATC
TGGACGGCCAACCGCCATGTGATGTAAGCCTCCATACGAAAGCACTGTTGCAGATAGAAG
AAGAGGTGGTTGCTGCTCATGTAGATCTATAAATATGTGTTGTATGTCTTTTTTGCTTTT
TTTTAAAAAAAAGAATAACTTTTTTTGCCTCTTTAGATTACATAGAAGCATTGTAGTCT
TGGTAGAACCAGTATTTTTGTTGTTTATTTATAAGGTAATTGTGTGTGGGGAAAAGTGCA
GTATTTACCTGTTGAATTCAGCATCTTGAGAGCACAAGGGAAAAAATAAGAACCTACGAA
TATTTTTGAGGCAGATAATGATCTAGTTTGACTTTCTAGTTAGTGGTGTTTTGAAGAGGG
TATTTTATTGTTTTTTAAAAAAAGGTTCTTAAACATTATTTGAAATAGTTAATATAAATA
CATAATTGCATTTGCTCTGTTTATTGTAATGTATTCTAAATTAATGCAGAACCATATGGA
AAATTTCATTAAAATCTATCCCCAAATGTGCTTTCTGTATCCTTCCTTCTACCTATTATT
CTGATTTTTAAAAATGCAGTTAATGTACCATTTATTTGCTTGATGAAGGGAGCTCTATTT
TCTTTACCAGAAATGTTGCTAAGTAATTCCCAATAGAAAGCTGCTTATTTTCATTAATGA
AAAATAACCATGGTTTGTATACTAGAAGTCTTCTTCAGAAACTGGTGAGCCTTTCTGTTC
AATTGCATTTGTAAATAAACTTGCTGATGCATTTAAAAAAAAAAAAAAAAA (SEQ ID
NO:1)

Figure 3A

ATAGCACGACTGTGTATGCTCTGGAGGACTGAAAGGCTGTACAAGCCCTATGTATTTTTT
TTCAAATATACATATGCATGGGTCTTGCTGCTGCCTCTTTTGCTGACTGTAATTGGACTT
TGAAGCTTCGAAGTTATATCATAAAAATTTGTAACCTTTGTCTGAGAGAGAGCTCAGCTA
AGCAATCACTTTCCACTTCTTTTCACAGGATAATATAAACGTTTTCTTGAAAGCTTGTGA
ACAGATTGGATTGAAAGAAGCCCAGCTTTTCCATCCTGGAGATCTACAGGATTTATCAAA
TCGAGTCACTGTCAAGCAAGAAGAGACTGACAGGAGAGTGAAAATGTTTTGATAACATT
GTACTGGCTGGGAAGAAAAGCACAAAGCAACCCGTACTATAATGGTCCCCATCTTAATTT
GAAAGCGTTTGAGAATCTTTTAGGACAAGCACTGACGAAGGCACTCGAAGACTCCAGCTT
CCTGAAAAGAAGTGGCAGGGACAGTGGCTACGGTGACATCTGGTGTCCTGAACGTGGAGA
ATTTCTTGCTCCTCCAAG**GCACCATAAGAGAGAAGATTCCTTTGAAAGCTTGGACTCTTT
GGGCTCGAGGTCATTGACAAGCTGCTCCTCTGATATCACGTTGAGAGGGGGCGTGAAGG
TTTTGAAAGTGACACAGATTCGGAATTTACATTCAAGATGCAGGATTATAATAAAGATGA
TATGTCGTATCGAAGGATTTCGGCTGTTGAGCCAAAGACTGCGTTACCCTTCAATCGTTT
TTTACCCAACAAAAGTAGACAGCCATCCTATGTACCAGCACCTCTGAGAAAGAAAAAGCC
AGACAAACATGAGGATAACAGAAGAAGTTGGGCAAGCCCGGTTTATACAGAAGCAGATGG
AACATTTTCAAGactctttcaaaagatttatggtgagaatggGAGTAAGTCCATGAGTGA
TGTCAGCGCAGAAGATGTTCAAAACTTGCGTCAGCTGCGTTACGAGGAGATGCAGAAAAT
AAAATCACAATTAAAAGAACAAGATCAGAAATGGCAGGATGACCTTGCAAAATGGAAAGA
TCGTCGAAAAAGTTACACTTCAGATCT**GCAGAAGAAAAAGAAGAGAGAGAAGAAATTGA
AAAGCAGGCACTTGAGAAGTCTAAGAGAAGCTCTAAGACGTTTAAGGAAATGCTGCAGGA
CAGGGAATCCCAAAATCAAAGTCTACAGTTCCGTCAAGAAGGAGAATGTATTCTTTTGA
TGATGTGCTGGAGGAAGGAAAGCGACCCCTACAATGACTGTGTCAGAAGCAAGTTACCA
GAGTGAGAGAGTAGAAGAGAAGGGAGCAACTTATCCTTCAGAAATTCCCAAAGAAGATTC
TACCACTTTTGCAAAAAGAGAGGACCGTGTAACAACTGAAATTCAGCTTCCTTCTCAAAG
TCCTGTGGAAGAACAAAGCCCAGCCTCTTTGTCTTCTCTGCGTTCACGGAGCACACAAAT
GGAATCAACTCGTGTTTCAGCTTCTCTCCCAGAAGTTACCGGAAAACTGATACAGTCAG
GTTAACATCTGTGGTCACACCAAGACCCTTTGGCTCTCAGACAAGGGGAATCTCATCACT
CCCCAGATCTTACACGATGGATGATGCTTGGAAGTATAATGGAGATGTTGAAGACATTAA
GAGAACTCCAAACAATGTGGTCAGCACCCCTGCACCAAGCCCGGACGCAAGCCAACTGGC
TTCAAGCTTATCTAGCCAGAAAGAGGTAGCAGCAACAGAAGAAGATGTGACAAGGCTGCC
CTCTCCTACATCCCCCTTCTCATCTCTTTCCCAAGACCAGGCTGCCACTTCTAAAGCCAC
ATTGTCTTCCACATCTGGTCTTGATTTAATGTCTGAATCTGGAGAAGGGGAAATCTCCCC
ACAAAGAGAAGTCTCAAGATCCCAGGATCAGTTCAGTGATATGAGAATCAGCATAAACCA
GACGCCTGGGAAGAGTCTTGACTTTGGGTTTACAATAAAATGGGATATTCCTGGGATCTT
CGTAGCATCAGTTGAAGCAGGTAGCCCAGCAGAATTTTCTCAGCTACAAGTAGATGATGA
AATTATTGCTATTAACAACACCAAGTTTTCATATAACGATTCAAAAGAGTGGGAGGAAGC
CATGGCTAAGGCTCAAGAAACTGGACACCTAGTGATGGATGTGAGGCGCTATGGAAAGGC
TGGTTCACCTGAAACAAAGTGGATTGATGCAACTTCTGGAATTTACAACTCAGAAAAATC
TTCAAATCTATCTGTAACAACTGATTTCTCCGAAAGCCTTCAGAGTTCTAATATTGAATC
CAAAGAAATCAATGGAATTCATGATGAAAGCAATGCTTTTGAATCAAAAGCATCTGAATC
CATTTCTTTGAAAAACTTAAAAAGGCGATCACAATTTTTTGAACAAGGAAGCTCTGATTC
GGTGGTTCCTGATCTTCCAGTTCCAACCATCAGTGCCCCGAGTCGCTGGGTGTGGGATCA
AGAGGAGGAGCGGAAGCGGCAGGAGAGGTGGCAGAAGGAGCAGGACCGCCTACTGCAGGA
AAAATATCAACGTGAGCAGGAGAAACTGAGGGAAGAGTGGCAAAGGGCCAAACAGGAGGC

Figure 3B

```
AGAGAGAGAGAATTCCAAGTACTTGGATGAGGAACTGATGGTCCTAAGCTCAAACAGCAT
GTCTCTGACCACACGGGAGCCCTCTCTTGCCACCTGGGAAGCTACCTGGAGTGAAGGGTC
CAAGTCTTCAGACAGAGAAGGAACCCGAGCAGGAGAAGAGGAGAGGAGACAGCCACAAGA
GGAAGTTGTTCATGAGGACCAAGGAAAGAAGCCGCAGGATCAGCTTGTTATTGAGAGAGA
GAGGAAATGGGAGCAACAGCTTCAGGAAGAGCAAGAGCAAAAGCGGCTTCAGGCTGAGGC
TGAGGAGCAGAAGCGTCCTGCGGAGGAGCAGAAGCGCCAGGCAGAGATAGAGCGGGAAAC
ATCAGTCAGAATATACCAGTACAGGAGGCCTGTTGATTCCTATGATATACCAAAGACAGA
AGAAGCATCTTCAGGTTTTCTTCCTGGTGACAGGAATAAATCCAGATCTACTACTGAACT
GGATGATTACTCCACAAATAAAAATGGAAACAATAAATATTTAGACCAAATTGGGAACAC
GACCTCTTCACAGAGGAGATCCAAGAAGAACAAGTACCATCAGGAGCAGAATTGGAGAG
GCAACAAATCCTTCAGGAAATGAGGAAGAGAACACCCCTTCACAATGACAACAGCTGGAT
CCGACAGCGCAGTGCCAGTGTCAACAAAGAGCCTGTTAGTCTTCCTGGGATCATGAGAAG
AGGCGAATCTTTAGATAACCTGGACTCCCCCGATCCAATTCTTGGAGACAGCCTCCTTG
GCTCAATCAGCCCACAGGATTCTATGCTTCTTCCTCTGTGCAAGACTTTAGTCGCCCACC
ACCTCAGCTGGTGTCCACATCAAACCGTGCCTACATGCGGAACCCCTCCTCCAGCGTGCC
CCCACCTTCAGCTGGCTCCGTGAAGACCTCCACCACAGGTGTGGCCACCACACAGTCCCC
CACCCCGAGAAGCCATTCCCCTTCAGCTTCACAGTCAGGCTCTCAGCTGCGTAACAGGTC
AGTCAGTGGGAAGCGCATATGCTCCTACTGCAATAACATTCTGGGCAAAGGAGCCGCCAT
GATCATCGAGTCCCTGGGTCTTTGTTATCATTTGCATTGTTTAAGTGTGTTGCCTGTGA
GTGTGACCTCGGAGGCTCTTCCTCAGGAGCTGAAGTCAGGATCAGAAACCACCAACTGTA
CTGCAACGACTGCTATCTCAGATTCAAATCTGGACGGCCAACCGCCATGTGATGTAAGCC
TCCATACGAAAGCACTGTTGCAGATAGAAGAAGAGGTGGTTGCTGCTCATGTAGATCTAT
AAATATGTGTTGTATGTCTTTTTTGCTTTTTTTTAAAAAAAAGAATAACTTTTTTTGCC
TCTTTAGATTACATAGAAGCATTGTAGTCTTGGTAGAACCAGTATTTTGTTGTTTATTT
ATAAGGTAATTGTGTGTGGGGAAAAGTGCAGTATTTACCTGTTGAATTCAGCATCTTGAG
AGCACAAGGGAAAAAATAAGAACCTACGAATATTTTTGAGGCAGATAATGATCTAGTTTG
ACTTTCTAGTTAGTGGTGTTTTGAAGAGGGTATTTTATTGTTTTTAAAAAAAGGTTCTT
AAACATTATTTGAAATAGTTAATATAAATACATAATTGCATTTGCTCTGTTTATTGTAAT
GTATTCTAAATTAATGCAGAACCATATGGAAAATTTCATTAAAATCTATCCCCAAATGTG
CTTTCTGTATCCTTCCTTCTACCTATTATTCTGATTTTAAAAATGCAGTTAATGTACCA
TTTATTTGCTTGATGAAGGGAGCTCTATTTTCTTTACCAGAAATGTTGCTAAGTAATTCC
CAATAGAAAGCTGCTTATTTTCATTAATGAAAAATAACCATGGTTTGTATACTAGAAGTC
TTCTTCAGAAACTGGTGAGCCTTTCTGTTCAATTGCATTTGTAAATAAACTTGCTGATGC
ATTTAAAAAAAAAAAAAAAAAA  (SEQ ID NO:3)
```

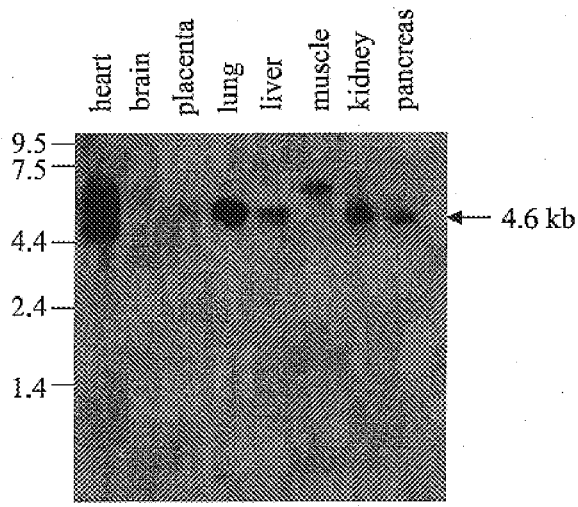
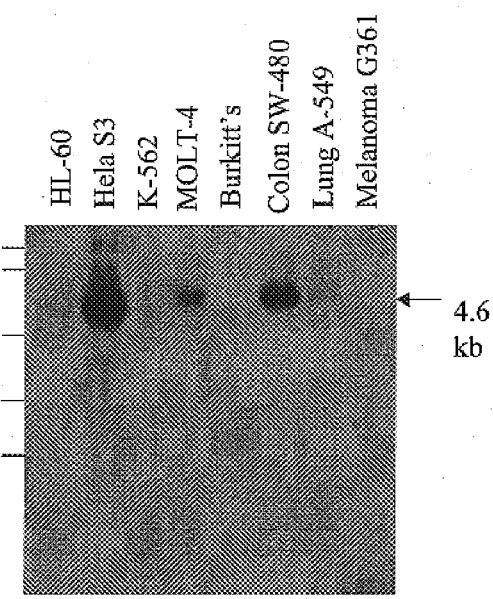
Figure 4    Probe: 2004-6    Figure 5

Human Tumor mRNA Northern Blot

Breast     Colon

T T T N    T T T N

Probe: 2004-6     ← 4.6 kb

Probe: β-actin     ← 1.8 kb

Figure 6

Figure 7    Probe: 2004-6

Figs. 9A-9D
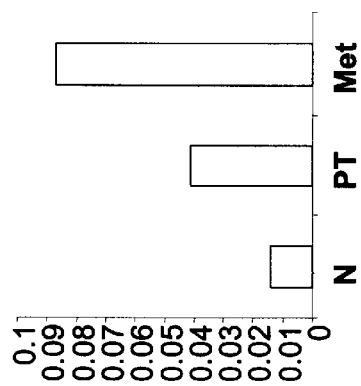
Fig. 9A
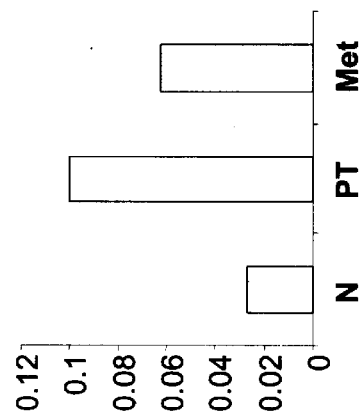
Fig. 9B
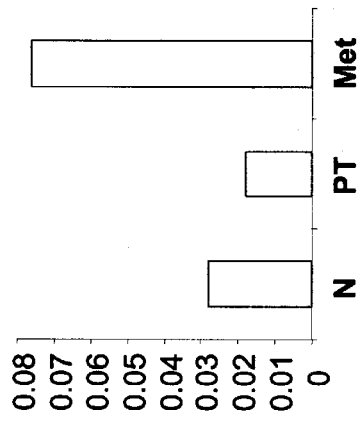
Fig. 9C
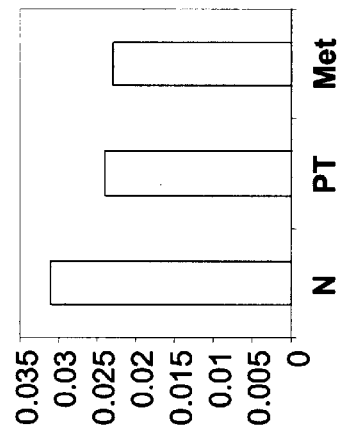
Fig. 9D Figs. 9E-9H
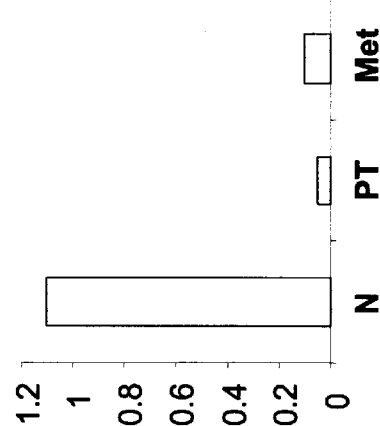
Fig. 9E
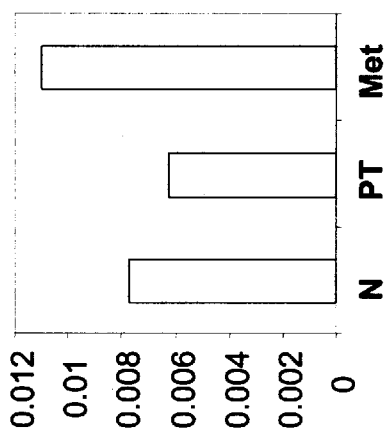
Fig. 9F
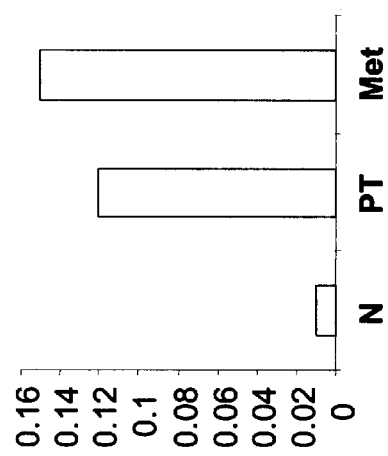
Fig. 9G
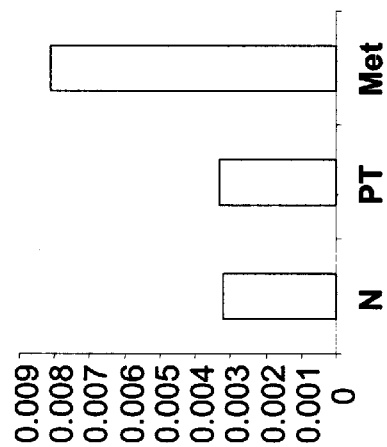
Fig. 9H

POLYNUCLEOTIDES DIFFERENTIALLY EXPRESSED IN ADENOCARCINOMAS, POLYPEPTIDES ENCODED THEREBY, AND METHODS OF USE THEREOF

CROSS-REFERENCE TO RELATED APPLICATIONS

This application claims the benefit of prior U.S. Provisional Application Serial No. 60/145,612, filed Jul. 26, 1999, now abandoned, and of prior U.S. Provisional Application Serial No. 60/148,936, filed Aug. 13, 1999 now abandoned.

FIELD OF THE INVENTION

The invention relates generally to novel polynucleotides, particularly those that are differentially expressed in cancer, in particular, pancreas, colon, and breast cancer.

BACKGROUND OF THE INVENTION

Pancreatic Cancer

Cancer of the pancreas is the fifth leading cause of cancer death in the United States. According to the American Cancer Society, approximately 28,000 people will die of pancreatic cancer in the United States in 1998. The pancreas is a tongue-shaped glandular organ composed of both endocrine and exocrine gland portions, as well as ducts that connect the pancreas to the bile duct and small intestine. The endocrine portion of the pancreas secretes hormones, such as insulin and glucagon, which are involved in blood sugar regulation, into the bloodstream. The exocrine portion of the pancreas produces pancreatic enzymes involved in the digestion of fats and proteins; these enzymes are delivered to the bile duct and into the small intestine.

Tumors of the endocrine pancreas have unique biological characteristics, and therapy is relatively effective. Neoplasms of the exocrine pancreas develop insidiously, and therapy is relatively ineffective. When considered by histological type, ductal cell adenocarcinomas are the most frequent type of exocrine pancreas tumors, accounting for approximately 82% of all tumors of the exocrine pancreas.

Although early and accurate diagnosis can thus be extremely important in treatment success, conventional screening tests for detecting pancreatic cancer in asymptomatic persons are inadequate. Imaging procedures such as magnetic resonance imaging and computed tomography are too costly to use as routine screening tests, while more accurate tests such as endoscopic retrograde cholangiopancreatography (ERCP) and endoscopic ultrasound are inappropriate for screening asymptomatic patients due to their invasiveness. Abdominal ultrasonography is a noninvasive screening test, but there is little information on the efficacy of abdominal ultrasound as a screening test for pancreatic cancer in asymptomatic persons. In symptomatic patients with suspected disease it has a reported sensitivity of 40–98% and a specificity as high as 90–94%. Conventional ultrasonography is limited by visualization difficulties in the presence of bowel gas or obesity and by its range of resolution (2–3 cm). Even tumors less than 2 cm in diameter are frequently associated with metastatic disease, thus limiting the ability of ultrasound to detect early disease.

Most persons with pancreatic malignancy have elevated levels of certain serologic markers such as CA19-9, peanut agglutinin, pancreatic oncofetal antigen, DU-PAN-2, carcinoembryonic antigen, alpha-fetoprotein, CA-50, SPan-1, and tissue polypeptide antigen (Rhodes et al. (1990) *Bailleres Clin. Gastroenterol.* 4:833; Steinberg (1990) *Am. J. Gastroenterol.* 85:350; Satake et al. (1990) *Int. J. Pancreatol.* 7:25; Satake (1991) *Int. J. Pancreatol.* 9:93). None of these markers is, however, tumor specific or organ specific (Satake (1991), supra). Elevations of various serologic markers also occur in significant proportions of persons with benign gastrointestinal diseases or malignancies other than pancreatic cancer (Carter (1990) *Gut* 31:494; Rhodes et al. (1990), supra; Satake et al. (1990), supra; Satake (1991), supra). Most of these markers have been studied exclusively in high-risk populations, such as symptomatic patients with suspected pancreatic cancer. CA19-9 has probably achieved the widest acceptance as a serodiagnostic test for pancreatic carcinoma in symptomatic patients, with an overall sensitivity of approximately 80% (68–93%) and specificity of 90% (73–100%); sensitivity was highest in patients with more advanced disease (Steinberg (1990), supra; Satake et al. (1990), supra). Among healthy subjects, CA19-9 has good specificity (94–99%) (DelVillano et al. (1983) *Clin. Chem.* 29:549; Ritts et al. (1984) *Int. J. Cancer* 33:339; Fabris et al. (1988) *Am. J. Gastroentrol.* 83:549) but nevertheless generates a large proportion of false-positive results due to the very low prevalence of pancreatic cancer in the general population (Frebourg et al. (1988) *Cancer* 62:2287; Homma et al. (1991) *Int. J. Pancreatol.* 9:119). The predictive value of a positive test could be improved if a population at substantially higher risk could be identified.

Breast Cancer

Breast cancer is the most common malignant neoplasm in women worldwide. This is also true in the United States, where the annual incidence was 104.6 new cases per 100,000 in 1989. The lifetime risk of breast cancer in the United States is estimated to be about one case for every eight women. Most breast cancers are invasive adenocarcinomas arising from the ductal lobular epithelial unit (Fisher (1975) *Cancer* 36:1), and the vast majority of patients have infiltrating ductal carcinomas. Overall, breast cancer makes up 32 percent of all cancer in U.S. women. The annual mortality rate from breast cancer has remained at about 27 deaths per 100,000 for many years despite improvements in medical management (*Cancer Treatment*, 4$^{th}$ Ed. C. Haskell, ed. (1995) W.B. Saunders Co). Current treatments include surgical resection, ionizing radiation therapy, systemic chemotherapy, endocrine therapy, or a combination of the foregoing.

Early diagnosis is of paramount importance in reducing mortality. Currently, screening and diagnostic methods include mammography and self-examination. Certain serum markers may be indicative of metastasis. Serial measurements of serum calcium and alkaline phosphatase are of established value for monitoring patients with known metastatic disease. Carcinoembryonic antigen (CEA) has been used to assess the response of patients to chemotherapy. The role of other potential tumor markers, such as CA549 and CA15-3, is currently under investigation.

Colorectal Cancer

Colorectal cancer is a major health problem in most affluent countries. In the United States, it is the fourth most frequent site for a primary malignant neoplasm, with approximately 149,000 new cases and 56,000 deaths expected in 1994. The vast majority of primary colorectal malignant neoplasms are epithelial adenocarcinomas. Current treatments include surgical resection, and single-agent and combination chemotherapy.

Current screening and diagnostic methods include, for asymptomatic people, tests for occult blood in the stool and screening flexible sigmoidoscopy. For symptomatic patients, diagnostic tests include barium enema, colonoscopy, and ultrasound.

Inadequacies of conventional diagnostic methods for the above-mentioned cancers highlight the need for diagnostic and therapeutic methods and compositions, as well as for a better understanding of the disease to provide the basis for more rationale and more quickly responsive therapy. The present invention addresses this need by providing nucleotide sequence that are differentially expressed in these diseases.

Related Literature

A human mRNA, designated "KIAA0858", was identified in human brain tissue, and is described in Nagase et al. (1998) *DNA Res.* 5:355–364. The nucleotide sequence of KIAA0858 is provided under GenBank Accession No. AB020665. A human mRNA was identified in pancreas tissue, its predicted translation product encodes a zinc-finger domain-containing protein, and its sequence is provided under GenBank Accession No. U90654.

SUMMARY OF THE INVENTION

The present invention is based on the discovery of polynucleotides that represent a gene that is differentially expressed in restricted types of cancer cells, specifically, colon, breast, and pancreatic cancer cells, particularly cancerous colon, breast, and pancreatic ductal epithelial cells. The present invention features a human HX2004-6 polypeptide and nucleotide sequences encoding HX2004-6 polypeptides. In a particular aspect, the polynucleotide is the nucleotide sequence of SEQ ID NO:1 and SEQ ID NO:3. In addition, the invention features polynucleotide sequences that hybridize under stringent conditions to SEQ ID NO:1 or SEQ ID NO:3. In related aspects the invention features expression vectors and host cells comprising polynucleotides that encode a human HX2004-6 polypeptide. The present invention also provides antibodies that bind specifically to a human HX2004-6 polypeptide.

The invention further provides methods using the polynucleotides and antibodies of the invention. The methods include methods for producing human HX2004-6 polypeptides; methods for detecting the presence of an HX2004-6 polypeptide or an HX2004-6 polynucleotide in a biological sample; methods for detecting cells expressing HX2004-6; methods for identification of individuals at risk for pancreatic, colon, or breast cancer by detecting alteration in HX2004-6 coding and regulatory sequences and HX2004-6 expression levels.

Another object of the invention is to provide an isolated human HX2004-6 polypeptide-encoding polynucleotide for use in generation of non-human transgenic animal models for HX2004-6 gene function, particularly "knock-in" HX2004-6 non-human transgenic animals characterized by excess or ectopic expression of the HX2004-6 gene.

The invention further provides screening methods to identify agents that modulate expression of human HX2004-, for example, transcription and/or translation of a human HX2004-6 polynucleotide. Of particular interest are those compounds that reduce human HX2004-expression, which compounds can be further evaluated for use in treating adenocarcinomas of breast, colon and pancreatic ductal epithelial cell origin.

These and other objects, advantages and features of the present invention will become apparent to those persons skilled in the art upon reading the details of the invention more fully set forth below.

The invention will now be described in further detail.

BRIEF DESCRIPTION OF THE DRAWINGS

FIGS. 2A–B depict the nucleotide sequence of HX2004-6 cDNA clone 1 (SEQ ID NO:1). For convenience, FIGS. 2A–B are referred to herein as "FIG. 2". The initiation codon and stop codons, ATG and TGA, respectively, are shown, in bold and underlined.

FIGS. 3A–B depict the nucleotide sequence of HX2004-6 cDNA clone 2 (SEQ ID NO:3). For convenience, FIGS. 3A–B are referred to herein as "FIG. 3". The sequence which is the 2004-6 probe (SEQ ID NO:5) is shown as a bold sequence. Within the 2004-6 sequence is the 30-nucleotide insertion (underlined and in lower case letters) relative to SEQ ID NO:1. The initiation codon and stop codons, ATG and TGA, respectively, are shown, in bold and underlined.

FIG. 4 depicts an autoradiograph of a human multiple tissue Northern blot probed with PCR-2004. RNA was from the following tissues: Lane 1, heart; Lane 2, brain; Lane 3, placenta; Lane 4, lung; Lane 5, liver; Lane 6, skeletal muscle; Lane 7, kidney; Lane 8, pancreas.

FIG. 5 depicts an autoradiograph of a human multiple cancer cell line Northern blot probed with PCR-2004. Cell lines were as follows: Lane 1, HL-60 (promyelocytic leukemia); Lane 2, HeLa cell S3; Lane 3, K-562 (chronic myelogenous leukemia); Lane 4, MOLT-4 (acute lymphoblastic leukemia); Lane 5, Raji (Burkitt's lymphoma); Lane 6, SW480 (colorectal adenocarcinoma); Lane 7, A549 (lung carcinoma); Lane 8, G361 (melanoma).

FIG. 6 depicts an autoradiograph of a tumor mRNA Northern blot probed with the 2004-6 probe (upper panels) and, as a control, β-actin (lower panels). mRNA samples were from breast tumor (Left-hand panels; Lanes marked "T") and normal breast (Left-hand panels; Lane "N") tissues, and colon tumor (Right-hand panels; Lanes marked "T") and normal colon tissue (Right-hand panels; Lane "N"), as described in Example 4.

FIGS. 9A–9H (collectively referred to herein as FIG. 9) are a series of graphs showing HX2004-6 expression levels in tissues from eight colon cancer patients. N: normal colon tissue; PT: primary tumor colon tissue; MET: metastatic liver tissue. The expression data (on the Y axis) are adjusted by β-actin expression level and are thus relative values. All PCR reactions were performed in duplicate.

DETAILED DESCRIPTION OF THE INVENTION

Figure 1:
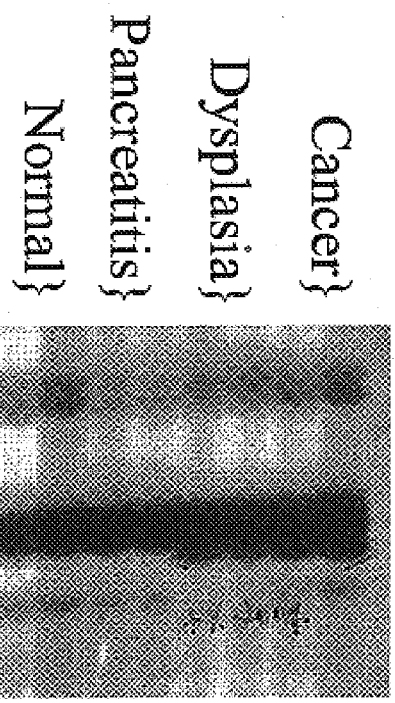
FIG. 1 depicts a sequencing gel autoradiograph of samples from a differential display assay. The arrow indicates the message differentially expressed in primary cultures of ductal epithelial cells from normal pancreas, and pancreas from individuals diagnosed with dysplasia of pancreatic cells, pancreatitis, and pancreatic cancer.

Before the present nucleotide and polypeptide sequences are described, it is to be understood that this invention is not limited to the particular methodology, protocols, cell lines, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a host cell" includes a plurality of such host cells and reference to "the antibody" includes reference to one or more antibodies and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, vectors, and methodologies which are described in the publications which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

Definitions

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" is used to refer to a specific polynucleotide sequence (e.g. a HX2004-6 polypeptide-encoding polynucleotide), "polynucleotide" is meant to encompass polynucleotides that encode a polypeptide that is functionally equivalent to the recited polypeptide, e.g., polynucleotides that are degenerate variants, or polynucleotides that encode biologically active variants or fragments of the recited polypeptide. Similarly, "polypeptide" as used herein refers to an oligopeptide, peptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule.

By "antisense polynucleotide" is mean a polynucleotide having a nucleotide sequence complementary to a given polynucleotide sequence (e.g, a polynucleotide sequence encoding an HX2004-6 polypeptide) including polynucleotide sequences associated with the transcription or translation of the given polynucleotide sequence (e.g., a promoter of a polynucleotide encoding an HX2004-6 polypeptide), where the antisense polynucleotide is capable of hybridizing to an HX2004-6 polypeptide-encoding polynucleotide sequence. Of particular interest are antisense polynucleotides capable of inhibiting transcription and/or translation of an HX2004-6-encoding polynucleotide either in vitro or in vivo.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen et al. (1993) *Anticancer Drug Des.* 8:53–63).

As used herein, "HX2004-6 polypeptide" refers to an amino acid sequence of a recombinant or nonrecombinant polypeptide having an amino acid sequence of i) a native HX2004-6 polypeptide, ii) a fragment of an HX2004-6 polypeptide, iii) polypeptide analogs of an HX2004-6 polypeptide, iv) variants of an HX2004-6 polypeptide, and v) an imunologically active fragment of an HX2004-6 polypeptide. HX2004-6 polypeptides of the invention can be obtained from any species, e.g., mammalian or non-mammalian (e.g., reptiles, amphibians, avian (e.g., chicken)), particularly mammalian, including human, rodent (e.g., murine or rat), bovine, ovine, porcine, murine, or equine, preferably rat or human, from any source whether natural, synthetic, semi-synthetic or recombinant. "Human HX2004-6 polypeptide" refers to the amino acid sequences of isolated human HX2004-6 polypeptide obtained from a human, and is meant to include all naturally-occurring allelic variants, and is not meant to limit the amino acid sequence to the complete, native amino acid sequence associated with the recited protein molecule.

The term "immunologically active" defines the capability of the natural, recombinant or synthetic human HX2004-6 polypeptide, or any oligopeptide thereof, to induce a specific immune response in appropriate animals or cells and to bind with specific antibodies.

As used herein, a "HX2004-6 associated disorder" is one that is associated with a neoplasm of pancreatic, colon, or breast cell, particularly an adenocarcinoma of one of these tissues, particularly a neoplasm of a ductal epithelial cell from one of these tissues. A "HX2004-6 associated disorder" is also one that is caused by, directly or indirectly, a neoplasm of one of the aforementioned cells. A "HX2004-6 associated disorder" is also a physiological condition or disease associated with altered HX2004-6 function (e.g., due to aberrant HX2004-6 expression, particularly overexpression of HX2004-6).

"Overexpression" intends that an HX2004-6 mRNA is found at levels at least about 1.5-fold, usually at least about 2-fold, normally at least about 5-fold, generally at least about 10-fold, and up to at least about 50-fold or higher when compared with a non-cancerous cell of the same cell type. In particular, the comparison is made between a ductal epithelial cell to be tested and a non-cancerous ductal epithelial cell, for example, a non-cancerous normal cell, or a dysplastic non-cancerous cell. The comparison can be made between two tissues, for example, if one is using in situ hybridization or another assay method which allows some degree of discrimination among cell types in the tissue, as described in Example 5; however, it may be preferable to make the comparison between cells removed from their tissue source, as described in Example 1. Whether an HX2004-6 polynucleotide is over-expressed in a given cell can be readily determined by those skilled in the art using known methods, including, but not limited to, detection of HX2004-6 transcripts by hybridization with a polynucleotide that hybridizes to a HX2004-6 polynucleotide, a polymerase chain reaction using specific oligonucleotide primers, in situ hybridization, by detection of encoded HX2004-6 polypeptide using an immunoassay, and the like.

As used herein, "neoplastic cells" and "neoplasia" (used interchangeably herein with "tumor", "cancer", "cancerous cells", and "carcinoma") refers to cells which exhibit relatively autonomous growth, so that they exhibit an aberrant growth phenotype characterized by a significant loss of control of cell proliferation. Neoplastic cells can be benign or malignant, metastatic or non-metastatic. The term "adenocarcinoma" is one well understood in the art, and denotes a tumor originating in glandular epithelium.

A "host cell", as used herein, denotes microorganisms or eukaryotic cells or cell lines cultured as unicellular entities which can be, or have been, used as recipients for recombinant vectors or other transfer polynucleotides, and include the progeny of the original cell which has been transfected.

It is understood that the progeny of a single cell may not necessarily be completely identical in morphology or in genomic or total DNA complement as the original parent, due to natural, accidental, or deliberate mutation. A host cell which comprises a recombinant vector of the invention is a "recombinant host cell".

As used herein, "antigenic amino acid sequence" means an amino acid sequence that, either alone or in association with a carrier molecule, can elicit an antibody response in a mammal.

A "variant" of a human HX2004-6 polypeptide is defined as an amino acid sequence that is altered by one or more amino acids. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, inserted or deleted without abolishing biological or immunological activity can be.found using computer programs well known in the art, for example, DNAStar software.

A "deletion" is defined as a change in either amino acid or nucleotide sequence in which one or more amino acid or nucleotide residues, respectively, are absent as compared to an amino acid sequence or nucleotide sequence of a naturally occurring HX2004-6 polypeptide.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring HX2004-6 polypeptide.

A "substitution" results from the replacement of one or more amino acids or nucleotides by different amino acids or nucleotides, respectively as compared to an amino acid sequence or nucleotide sequence of a naturally occurring HX2004-6 polypeptide.

The term "derivative" as used herein refers to the chemical modification of a nucleic acid encoding a human HX2004-6 polypeptide or the encoded human HX2004-6 polypeptide. Illustrative of such modifications would be replacement of hydrogen by an alkyl, acyl, or amino group. A nucleic acid derivative would encode a polypeptide which retains essential biological characteristics of a natural HX2004-6 polypeptide.

As used herein the term "isolated" is meant to describe a compound of interest (e.g., either a polynucleotide, a polypeptide, an antibody, or a cell) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

"Stringency" typically occurs in a range from about Tm-5° C. (5° C. below the Tm of the probe) to about 20° C. to 25° C. below Tm. As will be understood by those of skill in the art, stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs 1994 Dictionary of Biotechnology, Stockton Press, New York N.Y.). Amplification as carried out in polymerase chain reaction technologies is described in Dieffenbach et al. 1995, PCR Primer, a Laboratory Manual, Cold Spring Harbor Press, Plainview N.Y.

By "transformation" is meant a permanent or transient genetic change, preferably a permanent genetic change, induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

By "construct" is meant a recombinant nucleic acid, generally recombinant DNA, that has been generated for the purpose of the expression of a specific nucleotide sequence (s), or is to be used in the construction of other recombinant nucleotide sequences.

A "transcriptional control region" (sometimes referred to as a "transcriptional regulatory region") encompasses all the elements necessary for transcription, and may include elements necessary for transcription. Thus, a transcriptional control region includes at least the promoter sequence, and may also include other regulatory sequences such as enhancers, and transcription factor binding sites.

A "transcriptional control region heterologous to a coding region" is one that is not normally associated with the coding region in nature.

"Operably linked" refers to a juxtaposition wherein the components so described are in a relationship permitting them to function in their intended manner. For instance, a promoter is operably linked to a coding sequence if the promoter effects its transcription or expression.

"Regulatory sequences" refer to those sequences normally associated with (for example within 50 kb) of the coding region of a locus which affect the expression of the gene (including transcription of the gene, and translation, splicing, stability, or the like of the messenger RNA). Regulatory sequences include, inter alia, promoters, enhancers, splice sites and polyadenylation sites.

By "operatively inserted" is meant that a nucleotide sequence of interest is positioned adjacent a nucleotide sequence that directs transcription or transcription and translation of the introduced nucleotide sequence of interest (i.e., facilitates the production of, e.g., a polypeptide or a polynucleotide encoded by an HX2004-6 sequence).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. For particular methods described herein, such as diagnostic or screening methods, a biological sample of particular interest comprises ductal epithelial cells from pancreas, breast, and colon tissues. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

By "individual" or "subject" or "patient" is meant any mammalian subject for whom diagnosis or therapy is desired, particularly humans. Other subjects may include cattle, dogs, cats, guinea pigs, rabbits, rats, mice, horses, and so on. Of particular interest are subjects having an HX2004-6-associated disorder that is amenable to treatment (e.g., to mitigate symptoms associated with the disorder) by modulating expression of either HX2004-6-encoding nucleic acid in a cell of the subject.

The term "transgene" is used herein to describe genetic material which has been or is about to be artificially inserted into the genome of a mammalian, particularly a mammalian cell of a living animal.

By "transgenic organism" is meant a non-human organism (e.g., single-cell organisms (e.g., yeast), mammal, non-mammal (e.g., nematode or Drosophila)) having a non-endogenous (i.e., heterologous) nucleic acid sequence present as an extrachromosomal element in a portion of its cells or stably integrated into its germ line DNA.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

A "knock-out" of a target gene means an alteration in the sequence of the gene that results in a decrease of function of the target gene, preferably such that target gene expression is undetectable or insignificant. A knock-out of an HX2004-6 gene means that function of the HX2004-6 gene has been substantially decreased so that HX2004-6 expression is not detectable or only present at insignificant levels. "Knock-out" transgenics of the invention can be transgenic animals having a heterozygous knock-out of the HX2004-6 gene or a homozygous knock-out of the HX2004-6 gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased expression) of the target gene, e.g., by introduction of an additional copy of the target gene, or by operatively inserting a regulatory, sequence that provides for enhanced expression of an endogenous copy of the target gene. "Knock-in" transgenics of the invention can be transgenic animals having a heterozygous knock-in of the HX2004-6 gene or a homozygous knock-in of the HX2004-6 gene. "Knock-ins" also encompass conditional knock-ins.

As used herein, the term "treatment" encompasses any treatment of any disease or condition in a mammal, particularly a human, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., causing regression of the disease and/or its symptoms.

Overview of the Invention

The present invention is based upon the identification and isolation of a polynucleotide sequence encoding a human HX2004-6 polypeptide. Accordingly, the present invention encompasses such human HX2004-6 polypeptide-encoding polynucleotides, as well as human HX2004-6 polypeptides encoded by such polynucleotides. Overexpression of HX2004-6 is linked to adenocarcinomas of pancreas, colon, and breast, particularly neoplasms of ductal epithelial cells of pancreas, colon, and breast.

The present invention provides methods of detecting an HX2004-6 polynucleotide or polypeptide in a biological sample for diagnostic purposes. The invention also encompasses the use of the polynucleotides disclosed herein to facilitate identification and isolation of polynucleotide and polypeptide sequences having homology to a human HX2004-6 polynucleotide and polypeptide of the invention. The human HX2004-6 polypeptides and polynucleotides of the invention are also useful in the identification of human HX2004-6 polypeptide-binding compounds, particularly compounds which specifically bind human HX2004-6 polypeptide. Compounds which specifically bind HX2004-6 are useful in diagnostic assays to detect the presence of and/or measure a level of HX2004-6 polypeptide. In addition, the human HX2004-6 polypeptides, polynucleotides, and antibodies of the invention are useful in the diagnosis, prevention and treatment of disease associated with human HX2004-6 overexpression.

The human HX2004-6 polypeptide-encoding polynucleotides of the invention can also be used as a molecular probe with which to determine the structure, location, and expression of the human HX2004-6 polypeptide and related polypeptides in mammals (including humans), and to investigate potential associations between disease states or clinical disorders and defects or alterations in human HX2004-6 polypeptide structure, expression, or function.

The human HX2004-6 polynucleotides and antibodies specific for HX2004-6 polypeptides are also useful in screening assays to identify substances which modulate HX2004-6 expression in a cell.

HX2004-6 Nucleic Acid

The present invention provides isolated HX2004-6 nucleic acids. These nucleic acids are useful in methods to produce HX2004-6 polypeptides, as well as in diagnostic methods, including methods to detect an HX2004-6 mRNA in a biological sample, methods to identify polynucleotides having sequence similarity to HX2004-6 polynucleotides of the invention, methods to detect an alteration in HX2004-6 polynucleotide sequence in a cell, and methods to identify substances which modulate HX2004-6 mRNA and/or polypeptide levels in a cell.

In some embodiments, an HX2004-6 polynucleotide of the invention has the sequence shown in SEQ ID NO:1 (FIG. 2). In other embodiments, an HX2004-6 polynucleotide has the sequence shown in nucleotides 1–1724 of SEQ ID NO:1. In other embodiments, an HX2004-6 polynucleotide has the sequence shown in nucleotides 698–1724 of SEQ ID NO:1. In other embodiments, an HX2004-6 polynucleotide has the sequence shown in SEQ ID NO:3 (FIG. 3). In other embodiments, an HX2004-6 polynucleotide has the sequence shown in nucleotides 1–1754 of SEQ ID NO:3. In still other embodiments, an HX2004-6 polynucleotide has the sequence shown in nucleotides 728–1754 of SEQ ID NO:3. Also encompassed are the complement of any of the aforementioned sequences. Also encompassed by "HX2004-6 polynucleotide" are fragments of the aforementioned sequences. In one embodiment, a fragment of an HX2004-6 polynucleotide has the sequence of nucleotides 559 to 1107 of the sequence shown in SEQ ID NO:3, and shown in bold in FIG. 3. This sequence, which is given as SEQ ID NO:5 is also the sequence of the polynucleotide probe referred to herein as "the 2004-6 probe". Further encompassed are polynucleotides that hybridize under stringent hybridization conditions with any one of the aforementioned sequences, as described in detail herein. The invention also encompasses polypeptides encoded by any of the polynucleotide sequences described herein.

The term "HX2004-6 gene" is encompassed in the term "HX2004-6 polynucleotide" and is used generically to designate HX2004-6 genes and their alternate forms. "HX2004-6 gene" is also intended to mean the open reading frame encoding specific HX2004-6 polypeptides, introns, and adjacent 5' and 3' non-coding nucleotide sequences involved in the regulation of expression, up to about 1 kb beyond the coding region, but possibly further in either direction. The DNA sequences encoding HX2004-6 may be cDNA or genomic DNA or a fragment thereof. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing, to create a continuous open reading frame encoding the HX2004-6 polypeptide.

While other genomic HX2004-6 sequences of other sources may have non-contiguous open reading frames (e.g., where introns interrupt the protein coding regions), the human genomic HX2004-6 sequence has no introns interrupting the coding sequence. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where HX2004-6 is expressed. The sequences of the HX2004-6 promoter elements of the invention can be based on the nucleotide sequences of any species (e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably rat or human) and can be isolated or produced from any source whether natural, synthetic, semi-synthetic or recombinant.

As shown in Example 5, overexpression of HX2004-6 is restricted to neoplasms of pancreas, breast, and colon, particularly neoplasms of ductal epithelial cells of these tissues. The tissue-restricted overexpression of HX2004-6 is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. 1995 Mol Med 1:194–205; Mortlock et al. 1996 Genome Res. 6: 327–33; and Joulin and Richard-Foy (1995) Eur J Biochem 232: 620–626.

As shown in Example 5, HX2004-6 is overexpressed in certain cancer cells, namely pancreas, colon, and breast cancers, particularly adenocarcinomas, particularly cancerous ductal epithelial cells of these tissues. Accordingly, in some embodiments, HX2004-6 polynucleotides are overexpressed in exocrine pancreatic, colorectal, and/or breast cancer cells, particularly adenocarcinomas, particularly cancerous ductal epithelial cells of these cancers. "Overexpression" intends that an HX2004-6 mRNA is found at levels at least about 1.5-fold, normally at least about 2-fold, usually at least about 5-fold, generally at least about 10-fold, up to at least about 50-fold or higher when compared with a non-cancerous cell of the same cell type. Those skilled in the art can readily determine whether an HX2004-6 nucleic acid is overexpressed, using any known method, including Northern blot analysis, in situ hybridization, and the like, using an HX2004-6 nucleic acid of the invention or fragment thereof.

HX2004-6 regulatory sequences may be used to identify cis acting sequences required for transcriptional or translational regulation of HX2004-6 expression, especially in different tissues or stages of development, and to identify cis acting sequences and trans acting factors that regulate or mediate HX2004-6 expression. Such transcriptional or translational control regions may be operably linked to an HX2004-6 gene or other genes in order to promote expression of wild type or altered HX2004-6 or other proteins of interest in cultured cells, or in embryonic, fetal or adult tissues, and for gene therapy. HX2004-6 transcriptional or translational control regions can also be used to identify extracellular signal molecules that regulate HX2004-6 promoter activity, and thus regulate HX2004-6 expression.

The nucleic acid compositions used in the subject invention may encode all or a part of the HX2004-6 polypeptides as appropriate. SEQ ID NO:2 gives the amino acid translation of the nucleotide sequence given as SEQ ID NO:1. SEQ ID NO:4 gives the amino acid translation of the nucleotide sequence given as SEQ ID NO:3. In some embodiments, an HX2004-6 polynucleotide encodes a polypeptide having the amino acid sequence shown in SEQ ID NO:2. In other embodiments, an HX2004-6 polynucleotide encodes a polypeptide having the amino acid sequence shown as amino acids 1–342 of SEQ ID NO:2. In other embodiments, an HX2004-6 polynucleotide encodes a polypeptide having the amino acid sequence shown in SEQ ID NO:4. In other embodiments, an HX2004-6 polynucleotide encodes a polypeptide having the amino acid sequence given as amino acids 1–352 of SEQ ID NO:4. Also encompassed are HX2004-6 polynucleotides encoding variants, fragments and fusion proteins of the aforementioned polypeptides. Accordingly, the invention encompasses an HX2004-6 polynucleotide which encodes a polypeptide having an amino acid sequence of at least 5, usually at least about 15, usually at least about 30 or more contiguous amino acids of amino acids 1–342 of SEQ ID NO:2 or amino acids 1–352 of SEQ ID NO:4; variants of an HX200-46 polypeptide, particularly variants having conservative amino acid substitutions of the aforementioned fragments; and fusion proteins comprising any one of the aforementioned fragments and a heterologous polypeptide (i.e., a non-HX2004-6 polypeptide).

HX2004-6 nucleic acids can be obtained by chemical or biochemical synthesis, by recombinant DNA techniques, or by isolating the nucleic acids from a biological source. Fragments may be obtained of the DNA sequence by chemically synthesizing oligonucleotides in accordance with conventional methods, by restriction enzyme digestion, by amplification (e.g., by a polymerase chain reaction), etc. For the most part, DNA fragments will be of at least about ten contiguous nucleotides, usually at least about 15 nucleotides (nt), more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The HX2004-6 gene is isolated and obtained in substantial purity, generally as other than an intact mammalian chromosome. Usually, the DNA will be obtained substantially free of other nucleic acid sequences that do not include an HX2004-6 sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They can be used in methods to detect HX2004-6 mRNA in a biological sample, as described in more detail below.

They may also be used as probes for identifying homologs of HX2004-6. Mammalian homologs have substantial sequence similarity to one another, i.e. at least 75%, usually at least 90%, more usually at least 95% sequence identity. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J. Mol. Biol.* 215:403–10. For the purposes of this invention, sequence identity is determined by the Smith-Waterman homology search algorithm as implemented in MPSRCH program (Oxford Molecular). For the purposes of this invention, a preferred method of calculating percent identity is the Smith-Waterman algorithm, using the following. Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

Nucleic acids having sequence similarity are detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). Sequences sharing a high degree of nucleotide sequence identity may be determined by hybridization under high stringency conditions, for example, at 50° C. or higher and 0.1×SSC (15 mM saline/0.15 mM sodium citrate). By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, Drosophila, Caenhorabditis, etc.

The HX2004-6-encoding DNA may also be used to identify expression of the gene in a biological specimen. The manner in which one probes cells for the presence of particular nucleotide sequences, as genomic DNA or RNA, is well established in the literature and does not require elaboration here. mRNA may be isolated from a cell sample, or may be detected without being first isolated. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to an HX2004-6 sequence is indicative of HX2004-6 gene expression in the sample.

The HX2004-6 nucleic acid sequence may be modified for a number of purposes, particularly where they will be used intracellularly, for example, by being joined to a nucleic acid cleaving agent, e.g. a chelated metal ion, such as iron or chromium for cleavage of the gene; or the like.

The sequence of the HX2004-6 locus, including flanking promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two but generally not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of HX2004-6 polypeptides with other polypeptides, or to alter properties of the proteins that affect their function or regulation. Such modified HX2004-6 sequences can be used, for example, to generate transgenic animals.

Techniques for in vitro mutagenesis of cloned genes are known. Examples of protocols for scanning mutations may be found in Gustin et al., 1993 Biotechniques 14:22 ; Barany, 1985 Gene 37:111–23; Colicelli et al., 1985 Mol Gen Genet 199:537–9; and Prentki et al., 1984 Gene 29:303–13. Methods for site-specific mutagenesis can be found in Sambrook et al., 1989 Molecular Cloning: A Laboratory Manual, CSH Press, pp. 15.3–15.108; Weiner et al., 1993 Gene 126:35–41; Sayers et al.; 1992 Biotechniques 13:592–6; Jones and Winistorfer, 1992 Biotechniques 12:528–30; Barton et al., 1990 Nucleic Acids Res.

18:7349–55; Marotti and Tomich, 1989 Gene Anal. Tech. 6:67–70; and Zhu 1989 Anal. Biochem. 177:120–4.

Recombinant Vectors

The present invention further provides recombinant vectors comprising an HX2004-6 polynucleotide of the invention. Recombinant vectors are useful for propagation of the subject HX2004-6 polynucleotides (cloning vectors). They are also useful for effecting expression of an HX2004-6 polynucleotide in a cell. The choice of appropriate vector is well within the skill of the art. A wide variety of vectors, both cloning vectors and expression vectors, are known to those skilled in the art, have been described in, inter alia, Current *Protocols in Molecular Biology*, (F. M. Ausubel, et al., Eds. 1987, and updates), and can be used in the present invention. Many such vectors are available commercially.

The subject polynucleotides are generally propagated by placing an HX2004-6 polynucleotide in a vector. Viral and non-viral vectors can be used, including plasmids. The choice of plasmid will depend on the type of cell in which propagation is desired and the purpose of propagation. Certain vectors are useful for amplifying and making large amounts of the desired DNA sequence.

Other vectors are suitable for expression in cells in culture ("expression vectors"). These vectors will generally include regulatory sequences ("control sequences" or "control regions") which are necessary to effect the expression of an HX2004-6 polynucleotide to which they are operably linked. Still other vectors are suitable for transfer and expression in cells in a whole organism or person.

Host Cells

The present invention further provides isolated host cells comprising HX2004-6 polynucleotides of the invention. Suitable host cells include prokaryotes such as *E. coli, B. subtilis, S. cerevisiae;* and eukaryotic cells, including insect cells in combination with baculovirus vectors, yeast cells, such as Saccharomyces cerevisiae, or cells of a higher organism such as vertebrates, particularly mammals, e.g. COS 7 cells, may be used as the expression host cells. Host cells can be used for the purposes of propagating an HX2004-6 polynucleotide, for production of an HX2004-6 polypeptide, or in a screening method as described below.

HX2004-6 Transgenic Animals

The HX2004-6-encoding nucleic acids can be used to generate genetically modified non-human animals or site specific gene modifications in cell lines. The term "transgenic" is intended to encompass genetically modified animals having a deletion or other knock-out of HX2004-6 gene activity, having an exogenous HX2004-6 gene that is stably transmitted in the host cells, "knock-in" having altered HX2004-6 gene expression, or having an exogenous HX2004-6 promoter operably linked to a reporter gene. Of particular interest are homozygous and heterozygous knockouts of HX2004-6.

Transgenic animals may be made through homologous recombination, where the HX2004-6 locus is altered. Alternatively, a nucleic acid construct is randomly integrated into the genome. Vectors for stable integration include plasmids, retroviruses and other animal viruses, YACs (yeast artificial chromosomes), and the like. Of interest are transgenic mammals, preferably a mammal from a genus selected from the group consisting of Mus (e.g., mice), Rattus (e.g., rats), Oryctologus (e.g., rabbits) and Mesocricetus (e.g., hamsters). More preferably the animal is a mouse which is defective or contains some other alteration in HX2004-6 gene expression or function.

A "knock-out" animal is genetically manipulated to substantially reduce, or eliminate endogenous HX2004-6 function, preferably such that target gene expression is undetectable or insignificant. Different approaches may be used to achieve the "knock-out". A chromosomal deletion of all or part of the native HX2004-6 homolog may be induced. Deletions of the non-coding regions, particularly the promoter region, 3' regulatory sequences, enhancers, or deletions of gene that activate expression of the HX2004-6 genes. A functional knock-out may also be achieved by the introduction of an anti-sense construct that blocks expression of the native HX2004-6 gene (for example, see Li and Cohen (1996) Cell 85:319–329).

Conditional knock-outs of HX2004-6 gene function can also be generated. Conditional knock-outs are transgenic animals that exhibit a defect in HX2004-6 gene function upon exposure of the animal to a substance that promotes target gene alteration, introduction of an enzyme that promotes recombination at the target gene site (e.g., Cre in the Cre-loxP system), or other method for directing the target gene alteration.

For example, a transgenic animal having a conditional knock-out of HX2004-6 gene function can be produced using the Cre-loxP recombination system (see, e.g., Kilby et al. 1993 Trends Genet 9:413–421). Cre is an enzyme that excises the DNA between two recognition sequences, termed loxP. This system can be used in a variety of ways to create conditional knock-outs of HX2004-6. For example, two independent transgenic mice can be produced: one transgenic for an HX2004-6. sequence flanked by loxP sites and a second transgenic for Cre. The Cre transgene can be under the control of an inducible or developmentally regulated promoter (Gu et al. 1993 Cell 73:1155–1164; Gu et al. 1994 Science 265:103–106), or under control of a tissue-specific or cell type-specific promoter (e.g., a pancreas-specific promoter or brain tissue-specific promoter). The HX2004-6 transgenic is then crossed with the Cre transgenic to produce progeny deficient for the HX2004-6 gene only in those cells that expressed Cre during development.

Transgenic animals may be made having an exogenous HX2004-6 gene. For example, the transgenic animal may comprise a "knock-in" of an HX2004-6 gene, such that the host cell genome contains an alteration that results in altered expression (e.g., increased (including ectopic) or decreased expression) of an HX2004-6 gene, e.g., by introduction of an additional copy of the target gene, or by operatively inserting a regulatory sequence that provides for enhanced expression of an endogenous copy of the target gene. "Knock-in" transgenics can be transgenic animals having a heterozygous knock-in of the HX2004-6 gene or a homozygous knock-in of the HX2004-6. "Knock-ins" also encompass conditional knock-ins.

The exogenous gene introduced into the host cell genome to produce a transgenic animal is usually either from a different species than the animal host, or is otherwise altered in its coding or non-coding sequence. The introduced gene may be a wild-type gene, naturally occurring polymorphism, or a genetically manipulated sequence, for example those previously described with deletions, substitutions or insertions in the coding or non-coding regions. The introduced sequence may encode an HX2004-6 polypeptide, or may utilize the HX2004-6 promoter operably linked to a reporter gene. Where the introduced gene is a coding sequence, it is usually operably linked to a promoter, which may be constitutive or inducible, and other regulatory sequences required for expression in the host animal.

Specific constructs of interest include, but are not limited to, anti-sense HX2004-6, or a ribozyme based on an HX2004-6 sequence, which will block HX2004-6 expression, as well as expression of dominant negative HX2004-6 mutations, and over-expression of an HX2004-6 gene. A detectable marker, such as lac Z may be introduced into the HX2004-6 locus, where upregulation of expression of the HX2004-6 gene will result in an easily detected change in phenotype. Constructs utilizing a promoter region of the HX2004-6 genes in combination with a reporter gene or with the coding region of HX2004-6 are also of interest. Constructs having a sequence encoding a truncated or altered (e.g, mutated) HX2004-6 are also of interest.

The modified cells or animals are useful in the study of function and regulation of HX2004-6. Such modified cells or animals are also useful in, for example, the study of the function and regulation of genes whose expression is affected by HX2004. Thus, the transgenic animals of the invention are useful in identifying downstream targets of HX2004-6, as such targets may have a role in the phenotypes associated with overexpression of HX2004-6.

Animals may also be used in functional studies, drug screening, etc., e.g. to determine the effect of a candidate drug on HX2004-6 expression. A series of small deletions and/or substitutions may be made in the HX2004-6 genes to determine the role of different polypeptide-encoding regions in DNA binding, transcriptional regulation, etc. By providing expression of HX2004-6 protein in cells in which it is otherwise not normally produced (e.g., ectopic expression), one can induce changes in cell behavior.

DNA constructs for homologous recombination will comprise at least a portion of the HX2004-6 gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. 1990 Methods in Enzymology 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene. Chimeric animals having the modification (normally chimeric males) are mated with wild-type animals to produce heterozygotes, and the heterozygotes mated to produce homozygotes. If the gene alterations cause lethality at some point in development, tissues or organs can be maintained as allogeneic or congenic grafts or transplants, or in in vitro culture.

Investigation of genetic function may utilize non-mammalian models, particularly using those organisms that are biologically and genetically well characterized, such as *C. elegans, D. melanogaster* and *S. cerevisiae*. For example, transposon (Tc1) insertions in the nematode homolog of an HX2004-6 gene or a promoter region of an HX2004-6 gene may be made. The HX2004-6 gene sequences may be used to knock-out or to complement defined genetic lesions in order to determine the physiological and biochemical pathways involved in development of a neoplasm. It is well known that human genes can complement mutations in lower eukaryotic models.

HX2004-6 Polypeptides

The invention provides isolated HX2004-6 polypeptides and methods for making the polypeptides. HX2004-6 polypeptides include polypeptides having the sequences shown in SEQ ID NO:2 and SEQ ID NO:4, amino acids 1–342 of SEQ ID NO:2, amino acids 1–352 of SEQ ID NO:4; variants thereof, particularly variants comprising conservative amino acid substitutions; fragments thereof, particularly fragments having at least about 5, usually at least about 15, usually at least about 30 or more contiguous amino acids of the aforementioned sequences; and fusion proteins thereof. HX2004-6 polypeptides can be chemically synthesized, produced by recombinant methods, isolated from a biological source, or a combination of the foregoing.

HX2004-6-encoding nucleic acid may be employed to synthesize full-length HX2004-6 polypeptides or fragments thereof, for example, fragments at least about 8 amino acids in length, more usually at least about 15 amino acids in length, to about 25 amino acids, and up to the complete open reading frame of the HX2004-6 cDNA; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. In many situations, it may be desirable to express the HX2004-6 genes in mammalian cells, particularly isolated mammalian cells, especially where the encoded polypeptides will benefit from native folding and post-translational modifications. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

Antibodies Specific for HX2004-6 Polypeptides

The invention further provides isolated antibodies specific for HX2004-6 polypeptides of the invention. The HX2004-6 polypeptides can be used for the production of antibodies, where short fragments provide for antibodies specific for the particular polypeptide, and larger fragments or the entire protein allow for the production of antibodies over the surface of the polypeptide. Antibodies may be raised to the wild-type or variant forms of HX2004-6. Antibodies may be raised to isolated peptides corresponding to these domains, or to the native protein, e.g. by immunization with cells expressing HX2004-6, immunization with liposomes having HX2004-6 polypeptides inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli,* and the heavy and light chains mixed to further enhance the affinity of the antibody. Alternatives to in vivo immunization as a method of raising antibodies include binding to phage "display" libraries, usually in conjunction with in vitro affinity maturation.

Isolation of HX2004-6 Allelic Variants and Homologs in Other Species

Other mammalian HX2004-6 genes can be identified and isolated and their function characterized using the HX2004-6 genes used in the present invention. Other HX2004-6 genes of interest include, but are not limited to, mammalian (e.g., human, rodent (e.g, murine, or rat), bovine, feline, canine, and the like) and non-mammalian (e.g., chicken, reptile, and the like). Methods for identifying, isolating, sequencing, and characterizing an unknown gene based upon its homology to a known gene sequence are well known in the art (see, e.g., Sambrook et al., Molecular Cloning: A Laboratory Manual, CSH Press 1989.

Detection Methods Using HX2004-6 Polynucleotides and Antibodies of the Invention The present invention provides detection methods using HX2004-6 polynucleotides, and antibodies specific for HX2004-6 polypeptides of the invention. Detection methods using HX2004-6 polynucleotides include methods of detecting a level of HX2004-6 messenger RNA (mRNA) in a biological sample. These methods can be used to monitor HX2004-6 mRNA levels in response to a treatment, such as chemotherapy or radiation therapy, for treating pancreatic, breast, or colon cancer; to assess the efficacy of a drug in lowering HX2004-6 polynucleotide levels in a cell; to detect the presence of cells in an individual or in a culture which overexpress HX2004-6 mRNA, wherein the presence of a cell or cells which overexpress HX2004-6 mRNA is indicative of the presence of cancerous cells; in screening methods to detect agents which modulate levels of HX2004-6 mRNA; and to monitor progression of a cell from a normal to a neoplastic state. Detection methods to detect the presence of a HX2004-6 polynucleotide can also be used to detect a polymorphism in the HX2004-6 polynucleotide, which polymorphism may be indicative or predictive of a predisposition to develop pancreatic, breast, or colon cancer.

Similarly, the invention provides methods of detecting HX2004-6 polypeptides in a biological sample. These methods can be used to assess the efficacy of a drug in lowering HX2004-6 polypeptide levels in a cell; to detect the presence of cells in an individual or in a culture which overexpress HX2004-6 protein, wherein the presence of a cell or cells which overexpress HX2004-6 protein may be indicative of the presence of cancerous cells; in screening methods to detect agents which modulate levels of HX2004-6 polypeptides; and to monitor progression of a cell from a normal to a neoplastic state. Detection methods to detect the presence of a HX2004-6 polypeptide can also be used to detect the presence an abnormal HX2004-6 polypeptide, such as a truncated polypeptide, or other mutant HX2004-6 protein.

Methods of Detecting HX2004-6 mRNA in a Biological Sample

The present invention provides methods of detecting an HX2004-6 messenger RNA (mRNA) in a biological sample. Such methods are useful diagnostic methods to assess the potential of a cell to become neoplastic (where overexpression of HX2004-6 is an indication that a cell is, or is pre-disposed to become, neoplastic), to assess the efficacy of a chemotherapeutic regimen, as part of a screening method to identify agents that reduce the expression of HX2004-6 mRNA, and/or to detect the presence of a cell(s) which overexpress HX2004-6 mRNA. The methods generally involve contacting a biological sample with an HX2004-6 polynucleotide capable of hybridizing to an HX2004-6 mRNA, or the complement thereof as appropriate, and detecting hybridization. mRNA can be detected directly, or can first be reverse transcribed into cDNA for analysis. In addition, multiple copies of the mRNA can be made by amplification reactions, if desired.

mRNA may be isolated from a biological sample, or may be detected without being first isolated. Alternatively, the mRNA sample is separated by gel electrophoresis, transferred to a suitable support, e.g. nitrocellulose, nylon, etc., and then probed with all or a fragment of HX2004-6 cDNA as a probe, and detecting hybridization by Northern blotting, liquid hybridization techniques, and the like. Where mRNA is being directly hybridized to an HX2004-6 polynucleotide, the HX2004-6 polynucleotide comprises a sequence complementary to the HX2004-6 mRNA being detected.

Alternatively, mRNA may be amplified by. RT-PCR, using reverse transcriptase to form a complementary DNA strand, followed by a polymerase chain reaction amplification using primers specific for the subject DNA sequences.

For example, pancreatic cells may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. 1985 *Science* 239:487; a review of current techniques may be found in Sambrook, et al. Molecular Cloning: A Laboratory Manual, CSH Press 1989, pp.14.2–14.33.

In some instances, it may be desirable to analyze many samples at the same time for HX2004-6 mRNA expression levels. A variety of arrays have been described, and can be used in these methods. Quantitative monitoring of gene expression patterns with a complementary DNA microarray is described in Schena et al. (1995) *Science* 270:467. DeRisi et al. (1997) *Science* 270:680–686 explore gene expression on a genomic scale. Analysis of gene expression patterns in human cancer using a cDNA microarray is described in DeRisi et al. (1996) *Nat. Genet.* 14:457. Expression analysis using nucleic acid arrays is reviewed by Ramsay (1998) *Nat. Biotech.* 16:40–44. Methods for creating microarrays of biological samples, such as arrays of DNA samples to be used in DNA hybridization assays, are described in PCT publication no. WO 95/35505, published Dec. 28, 1995; U.S. Pat. No. 5,445,934; Drmanac et al., *Science* 260:1649; and Yershov et al. (1996) *Genetics* 93:4913. Use of differential display to identify differential gene expression is described in, for example, U.S. Pat. Nos. 5,776,683; and 5,807,680.

Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

Other techniques, such as oligonucleotide ligation assays, and in situ hybridizations, can also be used. In situ hybridization is described in a variety of textbooks, including, for example, Current Protocols in Molecular Biology, Ausubel et al., eds. For example, a fragment of HX2004-6 cDNA, particularly and oligonucleotide of about 18–30 nucleotides in length, can be labeled, for example, with biotin, and used to probe a tissue section. The tissue section can then be developed using an avidin-coupled enzyme and a substrate for the enzyme which yields a colored product. Counterstaining with, for example, hematoxylin and eosin, according to standard protocols, can be carried out.

In other embodiments, mRNA is detected by amplifying reverse-transcribed cDNA copies of the mRNA, using oligonucleotide primers that are detectably labeled. In these embodiments, a detectable label is included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product. Detection of the reverse-transcribed and amplified HX2004-6 mRNA is achieved by standard methods to detect, as appropriate, fluorescence, radioactivity, the product(s) of an enzymatic reaction, etc.

Overexpression of HX2004-6 mRNA is assessed relative to an appropriate control, e.g., a counterpart cell that is known to be normal, and/or a cell line of the same cell type which is known to have normal expression of HX2004-6 mRNA.

Methods of Detecting HX2004-6 Polypeptides in a Biological Sample

The present invention further provides methods of detecting HX2004-6 polypeptides in a biological sample. Antibodies specific for HX2004-6 polypeptides can be used in these detection methods. The methods generally comprise contacting a biological sample with an antibody specific for an HX2004-6 polypeptide, and detecting specific binding.

A sample is taken from a patient suspected of having an HX2004-6-associated disorder. Samples, as used herein, include tissue biopsies, biological fluids, organ or tissue culture derived fluids, and fluids extracted from physiological tissues, as well as derivatives and fractions of such fluids. If the polypeptide to be detected is associated with a cell, the number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

Diagnosis may be performed by a number of methods. The different methods all determine the absence or presence of HX2004-6 polypeptide in the biological sample being tested. For example, detection may utilize staining of cells or histological sections, performed in accordance with conventional methods. Antibodies specific for HX2004-6 polypeptides are added to the cell sample, and incubated for a period of time sufficient to allow binding to the epitope(s), usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and HX2004-6 polypeptides in a cell lysate or other biological fluid. Measuring the concentration of HX2004-6 binding in a sample or fraction thereof may be accomplished by a variety of specific assays. A conventional sandwich type assay may be used. For example, a sandwich assay may first attach HX2004-6-specific antibodies to an insoluble surface or support. The particular manner of binding is not crucial so long as it is compatible with the reagents and overall methods of the invention. They may be bound to the plates covalently or non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Cell lysates (or other biological fluid) are then added to separately assayable supports (for example, separate wells of a microtiter plate) containing antibodies. Preferably, a series of standards, containing known concentrations of normal and/or abnormal HX2004-6 is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hours is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second antibody is applied. The antibody will bind HX2004-6 with sufficient specificity such that it can be distinguished from other components present. The second antibodies may be labeled to facilitate direct, or indirect quantification of binding. Examples of labels that permit direct measurement of second receptor binding include radiolabels, such as $^3$H or $^{125}$I, fluorescers, dyes, beads, chemiluminescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for HX2004-6 as desired, conveniently using a labeling method as described for the sandwich assay. Antibody arrays may be formed wherein antibody specific for HX2004-6 polypeptide is attached to a solid support and, after allowing binding of a test sample, HX2004-6 polypeptide is detected using a detectably labeled antibody specific for HX2004-6 polypeptide.

Screening Assays

The transgenic animals, recombinant host cells, polynucleotides, and antibodies of the invention can be used to identify candidate agents that affect HX2004-6 expression (e.g., by affecting HX2004-6 promoter function) or that interact with HX2004-6 polypeptides. Agents of interest can include those that enhance, inhibit, regulate, or otherwise affect HX2004-6 expression. Of particular interest are agents that reduce expression of HX2004-6. Agents that reduce HX2004-6 expression can be used to, for example, treat or study disorders associated with overexpression of HX2004-6 (e.g., pancreatic, breast, and/or colon cancer. "Candidate agents" is meant to include synthetic molecules (e.g., small molecule drugs, peptides, or other synthetically produced molecules or compounds, as well as recombinantly produced gene products) as well as naturally occurring compounds (e.g., polypeptides, hormones, plant extracts, and the like). In the screening assays of the invention, results obtained with test substances are compared to results obtained with appropriate controls. An appropriate control is provided by conducting the assay in the absence of the test substance.

Drug Screening Assays

Of particular interest in the present invention is the identification of agents that have activity in affecting HX2004-6 expression and/or function. Such agents are candidates for development of treatments for, for example, cancer or other condition that may be associated with overexpression of HX2004-6. Drug screening identifies agents that provide for down-regulation of HX2004-6 expression or function in affected cells. Of particular interest are screening assays for agents that have a low toxicity for human cells.

The term "agent" as used herein describes any molecule, e.g. protein or pharmaceutical, with the capability of reducing expression of HX2004-6 and/or of reducing HX2004-6 polypeptide function. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening of Candidate Agents In Vivo

Agents can be screened for their ability to affect HX2004-6 expression or function or to mitigate an undesirable phenotype (e.g., a symptom) associated with an alteration in HX2004-6 expression or function. In some embodiments, screening of candidate agents is performed in vivo in a transgenic animal described herein. Transgenic animals suitable for use in screening assays include any transgenic animal having an alteration in HX2004-6 expression, and can include transgenic animals having, for example, an exogenous and stably transmitted human HX2004-6 gene sequence, a reporter gene composed of an isolated human HX2004-6 promoter sequence operably linked to a reporter gene (e.g,. β-galactosidase, CAT, luciferase, or other gene that can be easily assayed for expression), or a homozygous or heterozygous knockout of an HX2004-6 gene. The transgenic animals can be either homozygous or heterozygous for the genetic alteration and, where a sequence is introduced into the animal's genome for expression, may contain multiple copies of the introduced sequence. Where the in vivo screening assay is to identify agents that affect the activity of the HX2004-6 promoter, the HX2004-6 promoter can be operably linked to a reporter gene (e.g., luciferase) and integrated into the non-human host animal's genome.

The candidate agent is administered to a non-human, transgenic animal having altered HX2004-6 expression, and the effects of the candidate agent determined. The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent that approaches an upper limit of the amount that can be delivered successfully to the animal), and may include delivery of the agent in different formulation. The agents can be administered singly or can be combined in combinations of two or more, especially where administration of a combination of agents may result in a synergistic effect.

The effect of agent administration upon the transgenic animal can be monitored by assessing HX2004-6 function as appropriate (e.g., by examining expression of a reporter or fusion gene), or by assessing a phenotype associated with the HX2004-6 expression. For example, where the transgenic animal used in the screen exhibits overexpression of HX2004-6, the effect of the candidate agent can be assessed by determining levels of HX2004-6 mRNA produced in normal non-transgenic littermates and/or in wildtype mice Levels of HX2004-6 mmRNA can be measured using techniques that are well known in the art. Where the in vivo screening assay is to identify agents that affect the activity of the HX2004-6 promoter and the non-human transgenic animal (or cultured mammalian cell line) comprises an HX2004-6 promoter operably linked to a reporter gene, the effects of candidate agents upon HX2004-6 promoter activity can be screened by, for example, monitoring the expression from the HX2004-6 promoter (through detection of the reporter gene) and correlation of altered HX2004-6 promoter activity an aberrant cellular phenotype, such as aberrant mitotic activity, or other indications of neoplastic transformation. Alternatively or in addition, HX2004-6 promoter activity can be assessed by detection (qualitative or quantitative) of HX2004-6 mRNA or protein levels. Where the candidate agent affects HX2004-6 expression, and/or affects an HX2004-6-associated phenotype, in a desired manner, the candidate agent is identified as an agent which may be suitable for use in therapy of an HX2004-6-associated disorder in vivo.

Screening of Candidate Agents Using Cell-Based Assays

In addition to screening of agents in HX2004-6 transgenic animals, a wide variety of cell-based assays may be used for this purpose, using, for example, a mammalian cell transformed with a construct comprising HX2004-6 cDNA such that the cDNA is overexpressed, or, alternatively, a construct comprising an HX2004-6 promoter operably linked to a reporter gene.

Accordingly, the present invention provides a method for identifying an agent, particularly a biologically active agent, that modulates a level of human HX2004-6 expression in a cell, the method comprising: combining a candidate agent to be tested with a cell comprising a nucleic acid which encodes a human HX2004-6 polypeptide; and determining the effect of said agent on HX2004-6 expression. "Modulation" of HX2004-6 expression levels includes increasing the level and decreasing the level of HX2004-6 mRNA and/or HX2004-6 polypeptide encoded by the HX2004-6 polynucleotide when compared to a control lacking the agent being tested. An increase or decrease of about 1.25-fold, usually at least about 1.5-fold, usually at least about 2-fold, usually at least about 5-fold, usually at least about 10-fold or more, in the level (i.e., an amount) of HX2004-6 mRNA and/or polypeptide following contacting the cell with a candidate agent being tested, compared to a control to which no agent is added, is an indication that the agent modulates HX2004-6 expression.

An agent being tested for its effect on HX2004-6 expression is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2 H-tetrazolium bromide]) assay, and the like. Agents that do not exhibit cytotoxic activity are considered candidate agents.

The cells used in the assay are usually mammalian cells, including, but not limited to, rodent cells and human cells. The cells may be primary cultures of ductal epithelial cells, or may be immortalized cell lines.

HX2004-6 mRNA and/or polypeptide whose levels are being measured can be encoded by an endogenous HX2004-6 polynucleotide, or the HX2004-6 polynucleotide can be one that is comprised within a recombinant vector and introduced into the cell, i.e., the HX2004-6 mRNA and/or polypeptide can be encoded by an exogenous HX2004-6 polynucleotide. For example, a recombinant vector may comprise an isolated human HX2004-6 transcriptional regulatory sequence, such as a promoter sequence, operably linked to a reporter gene (e.g,. β-galactosidase, CAT, luciferase, or other gene that can be easily assayed for expression). In these embodiments, the method for identifying an agent that modulates a level of human HX2004-6 expression in a cell, comprises: combining a candidate agent to be tested with a cell comprising a nucleic acid which comprises a human HX2004-6 gene transcriptional regulatory element operably linked to a reporter gene; and determining the effect of said agent on reporter gene expression. A recombinant vector may comprise comprise an isolated human HX2004-6 transcriptional regulatory sequence, such as a promoter sequence, operably linked to sequences coding for an HX2004-6 polypeptide; or the transcriptional control sequences can be operably linked to coding sequences for an HX2004-6 fusion protein comprising HX2004-6 polypeptide fused to a polypeptide which facilitates detection. In these embodiments, the method comprises combining a candidate agent to be tested with a cell comprising a nucleic acid which comprises a human HX2004-6 gene transcriptional regulatory element operably linked to an HX2004-6 polypeptide-coding sequence; and determining the effect of said agent on HX2004 expression, which determination can be carried out by measuring an amount of HX2004-6 mRNA, HX2004-6 polypeptide, or HX2004-6 fusion polypeptide produced by the cell.

Cell-based assays generally comprise the steps of contacting the cell with an agent to be tested, forming a test sample, and, after a suitable time, assessing the effect of the agent on HX2004-6 expression. A control sample comprises the same cell without the candidate agent added. HX2004-6 expression levels are measured in both the test sample and the control sample. A comparison is made between HX2004-6 expression level in the test sample and the control sample. HX2004-6 expression can be assessed using conventional assays. For example, when a mammalian cell line is transformed with a construct that results in expression of HX2004-6, HX2004-6 mRNA levels can be detected and measured, as described above, or HX2004-6 polypeptide levels can be detected and measured, as described above. A suitable period of time for contacting the agent with the cell can be determined empirically, and is generally a time sufficient to allow entry of the agent into the cell and to allow the agent to have a measurable effect on HX2004-6 mRNA and/or polypeptide levels. Generally, a suitable time is between 10 minutes and 24 hours, more typically about 1–8 hours. Methods of measuring HX2004-6 mRNA levels are known in the art, several of which have been described above, and any of these methods can be used in the methods of the present invention to identify an agent which modulates HX2004-6 mRNA level in a cell, including, but not limited to, a PCR, such as a PCR employing detectably labeled oligonucleotide primers, and any of a variety of hybridization assays. Similarly, HX2004-6 polypeptide levels can be measured using any standard method, several of which have been described herein, including, but not limited to, an immunoassay such as ELISA, for example an ELISA employing a detectably labeled antibody specific for an HX2004-6 polypeptide.

The method described above is useful for identifying agents which may be useful in treating certain cancers. An agent which reduces HX2004-6 expression and is not cytotoxic is considered a possible agent for treatment of adenocarcinomas of pancreatic, breast, and colon ductal epithelial cell origin, e.g., to facilitate tumor regression, reduction in tumor mass, etc. Such agents are then further evaluated for safety and efficacy.

Screening of Candidate Agents Using Cell-Free Assays

Cell-free assays, i.e., assays which measure HX2004-6 polypeptide levels or function directly, include, but are not limited to, labeled in vitro protein-protein binding assays, protein-DNA binding assays, electrophoretic mobility shift assays, immunoassays for protein binding, and the like. Using these methods, one can identify substances that bind specifically to HX2004-6 polypeptides. Such substances are useful as diagnostic agents to detect the presence of and/or to measure a level of HX2004-6 polypeptide in a biological.

The screening assay can be a binding assay, wherein one or more of the molecules may be joined to a label, and the label directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g. albumin, detergents, etc that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Many mammalian genes have homologs in yeast and lower animals. The study of such homologs' physiological role and interactions with other proteins in vivo or in vitro can facilitate understanding of biological function. In addition to model systems based on genetic complementation, yeast has been shown to be a powerful tool for studying protein-protein interactions through the two hybrid system described in Chien et al. 1991 *Proc. Natl. Acad. Sci. USA* 88:9578–9582. Two-hybrid system analysis is of particular interest for exploring transcriptional activation by HX2004-6 proteins and to identify cDNAs encoding polypeptides that interact with HX2004-6.

Identified Candidate Agents

The compounds having the desired activity (i.e., modulation of HX2004-6 expression) may be administered in a physiologically acceptable carrier to a host for treatment of a condition attributable to overexpression of HX2004-6 (e.g., a neoplasm of a pancreatic, breast, or colon cell, particular an adenocarcinoma of one of these tissues). The therapeutic agents may be administered in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing Agents, wetting and emulsifying Agents, salts for varying the osmotic pressure or buffers for securing an adequate pH value, and skin penetration enhancers can be used as auxiliary agents.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is average molecular weight, temperature is in degrees Celcius, and pressure is at or near atmospheric.

Example 1

Identification of a Message Differentially Expressed in Pancreatic Cancer Cells

A family was identified that had several members who had been diagnosed with pancreatic cancer. The family members also have a form of diabetes. The pathological features of disease in the family included progression from normal to metaplasia to dysplasia to cancer. Tissues were obtained from a member of the family diagnosed with pancreatic cancer and from a member of the family diagnosed with dysplasia of pancreatic cells, and primary cultures of ductal cells prepared according to methods well known in the art. Tissue was also obtained from an unrelated person who was diagnosed with pancreatitis, and from an unrelated person who had a normal pancreas, and primary cultures of ductal cells prepared according to methods well known in the art.

The Genomyx HIEROGLYPH™ mRNA profile kit for differential display analysis was used according to the manufacturer's instructions to identify genes that are differentially expressed in the various samples relative to one another. Briefly, RNA was extracted from primary cultures of ductal epithelial cells obtained from patients with normal pancreas, nonspecific pancreatitis, pancreatic dysplasia and pancreatic carcinoma. Two μg of total RNA prepared by the guanidinium method was reverse-transcribed with anchored oligo-dT primer in a 10 μl reaction volume. Two μl of each reaction was subjected to PCR using 200 primer pairs to profile gene expression. [α-32P]dCTP (Amersham Pharmacia Biotech Inc., Piscataway, N.J.) was included in the PCR reaction. The PCR products were then separated on 6% sequencing gels using a GenomyxLR sequencer. The dried gels were subjected to autoradiography on Kodak BioMax films (33×61 cm).

The cDNA fragment pattern in each sample was manually compared to the cDNA fragment pattern in every other sample on the gel. The results, depicted in FIG. 1, show that cDNA 2004-6 (HX2004-6) is expressed in ductal epithelial cells of pancreatic tissue from individuals with pancreatic dysplasia and individuals with pancreatic cancer. In contrast, the transcript was not detectable in normal and pancreatitis samples. Thus, an alternative name assigned to the gene is PCD1 (pancreatic cancer-derived).

Example 2

Isolation and Sequencing of a Human HX2004-6 Polypeptide-Encoding Polynucleotide A band representing a differentially expressed gene product (i.e., a band associated with relatively more or less cDNA in one sample relative to another) was cut from the gel, amplified, cloned, and sequenced. The polynucleotide sequence of cDNA fragments isolated from one such differentially displayed cDNA fragment was identified as being differentially regulated in pancreatic disease and potentially other cancers. A cDNA library prepared from the human colon cell line HT29 was screened to isolate a full-length cDNA. This 4,612-nucleotide sequence ("clone 1") is given as SEQ ID NO:1 in the sequence listing, and depicted in FIG. 2. The predicted translation product of this polynucleotide is a 1054-amino acid polypeptide (provided as SEQ ID NO:2). Another clone ("clone 2") was sequenced, and was found to differ from the sequence shown in SEQ ID NO:1 by an insertion of 30 nucleotides (bold, underlined, lower-case lettering in FIG. 3). Its sequence is provided as SEQ ID NO:3 in the sequence listing. Translation of this polynucleotide predicts a translation product of 1064 amino acids (provided as SEQ ID NO:4). The deduced amino acid sequence contains a PDZ domain in the middle (amino acid residues 427–504) and a highly conserved LIM domain at the C-terminus (amino acid residues 995–1053) (FIG. 3).

PDZ domains (also called DHR or GLGF domains) are found in diverse membrane-proteins including members of the MAGUK family of guanylate kinase homologues, several protein phosphatases and kinases, neuronal nitric oxide synthase, and several dystrophin-associated proteins, collectively known as syntrophins. Many PDZ domain-containing proteins appear to be localized to highly specialized submembranous sites. LIM domains are cysteine-rich domains that bind zinc ions, and which act as the interface for protein-protein interaction. The LIM domain of HX2004-6 matched well with the LIM consensus motif $CX_2CX_{16-23}HX_2CX_2CX_2C_{16-21}CX_{2-3}(C/H/D)$.

Example 3

Comparison of SEQ ID NO:1 with Sequences in Database

The sequence given as SEQ ID NO:1 was used as a query sequence to search for similar sequences in GenBank, using the BLASTN (2.0.8) program with default parameters. Altschul et al. (1997) *Nucl. Acids. Res.* 25:3389–3402. A 2224-nucleotide sequence having 100% nucleotide identity with nucleotides 1725–3863 of SEQ ID NO:1 was identified. This sequence (GenBank Accession No. AB020665) is a human cDNA clone, from brain tissue, which encodes a polypeptide termed KIAA0858. Nagase et al. (1998) *DNA Res.* 5:355–364. Comparison of the predicted translation product of SEQ ID NO:1 with the translation product of the sequence found in GenBank revealed 100% amino acid sequence identity between amino acids 343–1054 of HX 2004-6 clone 1 polypeptide sequence and the KIAA0858 protein sequence.

Another sequence was found which shares 100% nucleotide sequence identity with nucleotides 2837–3863 of SEQ ID NO:1. This sequence (GenBank Accession No. U90654) is a partial cDNA sequence, from mRNA isolated from human pancreas, encoding a putative human zinc-finger domain. Comparison of the amino acid sequence revealed 100% amino acid sequence identity between amino acids 714–1054 of the predicted translation product of SEQ ID NO:1 and amino acids of the predicted translation product of U90654.

Example 4

Analysis of Tissue and Cell Type Distribution of 2004 Expression

To determine the tissue and cell type distribution of HX2004 expression, the HX2004 cDNA clone was used as a template for PCR to generate a radiolabeled probe corresponding to a portion of the cDNA clone. This radiolabeled fragment ("the PCR-2004 probe" or "the 2004-6 probe") was used to probe various RNA blots. This probe corresponds to nucleotides 559 to 1107 of SEQ ID NO:3, is denoted by bold lettering in FIG. 3, and is given here as SEQ ID NO:5.

When the 2004-6 probe was used as a hybridization probe with multiple tissue RNA blots (Clontech), a 4.6-kb band was observed in heart, placenta, lung, liver, kidney, and pancreas, as shown in FIG. 4. A band corresponding to an approximately 6-kb mRNA species was seen in heart, brain, lung, liver, and skeletal muscle. Thus, mRNA hybridizing with the 2004-6 probe is found in a variety of normal tissues. In addition, tissue-specific splicing event(s) may lead to messages of different lengths.

A multiple tissue RNA blot containing RNA from various cancer cell lines was hybridized with the 2004-6 probe (upper panels) and, to control for amount of RNA loaded per lane, a β-actin probe (lower panels). The results, depicted in FIG. 5, show that the 4.6-kb band was observed in HeLa, MOLT-4 (lymphoblastic leukemia), SW480 (colorectal adenocarcinoma), and faintly in A549 (lung carcinoma) cells.

To assess whether expression of HX2004 mRNA is associated with a particular cancerous state, a human tumor mRNA Northern blot (Invitrogen) was probed with the PCR-2004 probe. The data, presented in FIG. 6, show that the HX2004-6 message is detected in breast and colon tumors. Lanes marked "T" in the left-hand panels are breast tumor tissue samples. The first and third lanes marked "T" are invasive ductal carcinomas, while second lane marked "T" is a poorly differentiated invasive ductal carcinoma. Lane N in the left-hand panels is normal breast tissue. Lanes marked "T" in the right-hand panels are colon adenocarcinomas, and Lane N in the right-hand panels is normal colon tissue. HX2004-6 transcripts were also detected in normal tissues. This likely reflects the fact that the tissues used to prepare the human tumor material comprise many different cell types, including ductal epithelial cells.

Figure 7:
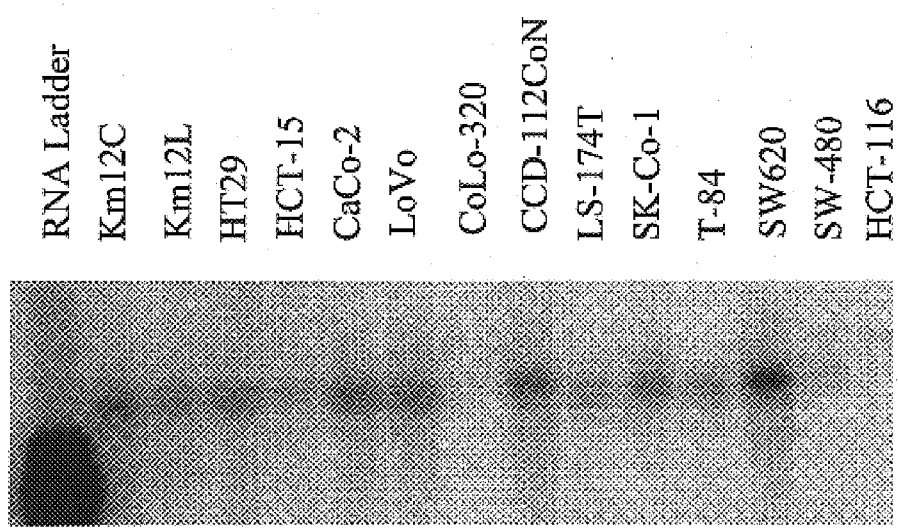
FIG. 7 depicts and autoradiograph of a colon cancer cell line RNA blot probed with the 2004-6 probe.

A variety of colon cancer cell lines were analyzed by Northern blot using the 2004-6 probe. The results, shown in FIG. 7, show that eight cell lines strongly express mRNA hybridizing with the 2004-6 probe; three cell lines show moderate levels of mRNA hybridizing with the 2004-6 probe; and three cell lines show low or undetectable expression of mRNA hybridizing with the 2004-6 probe.

Example 5

In situ Hybridization Analysis of HX2004-6 Expression in Breast, Pancreas, and Colon Cancer Tissue Sections In view of the fact that the tissue samples analyzed in the Northern analysis described in Example 4 comprise many different cell types, and thus would not assess differential expression in any one cell type, in situ hybridization analyses were conducted. Since these analyses use tissue sections, HX2004-6 expression levels in individual cell types can be evaluated.

Normal and cancerous tissue sections were obtained from colon, breast, liver, lung, pancreas, stomach, and prostate tissues using standard methods. The sections were fixed with 4% paraformaldehyde fixative, then overlaid with a mixture of oligonucleotide probes. corresponding to HX2004-6, as follows:

| Oligo #2 | 5'-GTAACTTTTTCGACGATCTTTCCAC-3' (SEQ ID NO:6) |
|---|---|
| Oligo #4 | 5'-TATTTTCTGCATCTCCTCGTAACGC-3' (SEQ ID NO:7) |
| Oligo #6 | 5'-TGACATCACTCATGGACTTACTCCC-3' (SEQ ID NO:8) |
| Oligo #8 | 5'-GTTCCATCTGCTTCTGTATAAACCG-3' (SEQ ID NO:9) |
| Oligo #13 | 5'-TCTGTTATCCTCATGTTTGTCTGGC-3' (SEQ ID NO:10) |
| Oligo #14 | 5'-TCTGGCTTTTTCTTTCTCAAAGTGC-3' (SEQ ID NO:11) |
| Oligo #16 | 5'-AAGTGCTGGTACATAGATGGCTGTC-3' (SEQ ID NO:12) |
| Oligo #18 | 5'-TCTACTTTTGTTGGGGTTGAAAACG-3' (SEQ ID NO:13) |
| Oligo #19 | 5'-TGTGTCACTTTCAAAAACTTCACGC-3' (SEQ ID NO:14) |
| Oligo #21 | 5'-AGAGCAGCTTGTCTATGAACTCCAG-3' (SEQ ID NO:15) |

The oligonucleotides were labeled with fluorescein isothiocyanate (FITC) according to standard procedures. Normal and cancerous tissue was stained with hematoxylin-eosin. Hybridization was detected using the Super Sensitive ISH Detection System kit from Biogenex Laboratories, Inc., San Ramon, Calif. All procedures were carried out as instructed in the protocol provided by the manufacturer.

Figure 8:
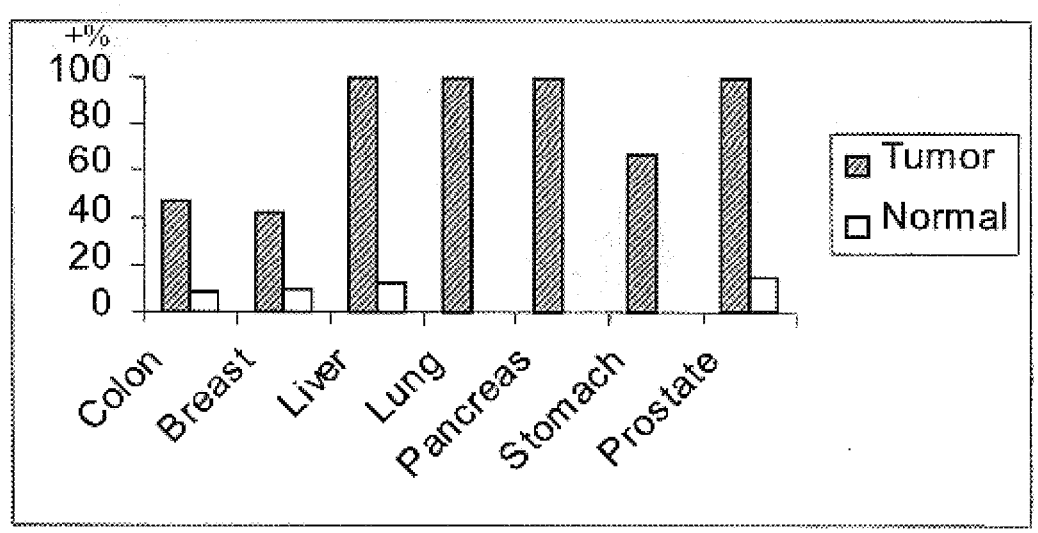
FIG. 8 is a graph showing the percentages of tumor and normal tissue samples expressing PCD1 by in situ hybridization analysis.

Table 1 summarizes the mRNA expression of HX2004-6 in 7 different tissues which we examined and FIG. 8 shows percentages of tissues which are positive for HX2004-6.

TABLE 1

Summary of HX2004–6 expression in tumor and normal tissues detected by in situ hybridization. =: srong expression; -: weak or no detectable expression

| Tissue | Tumor | | | Normal | | |
|---|---|---|---|---|---|---|
| | + | − | Total | + | − | Total |
| Colon | 65 | 73 | 138 | 4 | 44 | 48 |
| Breast | 76 | 103 | 179 | 3 | 26 | 29 |
| Liver | 51 | 0 | 51 | 1 | 7 | 8 |
| Lung | 20 | 0 | 20 | 0 | 8 | 8 |
| Pancreas | 7 | 0 | 7 | 0 | 4 | 4 |
| Stomach | 2 | 1 | 3 | 0 | 8 | 8 |
| Prostate | 4 | 0 | 4 | 2 | 12 | 14 |

For all seven tumor tissues, HX2004-6 expression is highly expressed in a significant portion of the samples tested; in contrast, few or none showed positive HX2004-6 expression in normal samples for each tissue. Therefore, HX2004-6 expression is elevated in a significant portion of tumor tissue samples from colon, breast, liver, lung, pancreas, stomach and prostate cancer patients.

Example 6

Expression Analysis by Real-time Quantitative RT-PCR

Real-time quantitative PCR was performed using a Lightcycler instrument to investigate expression levels of HX2004-6 message in tumor tissues from eight colon cancer patients.

One $\mu$g human placenta total RNA (Clontech, Palo Alto, Calif.) was reverse-transcribed with oligo-dT$_{18}$ primer at 42° C. for 1 hour then heated at 94° C. for 5 minutes in a total reaction volume of 20 $\mu$l (1st-Strand™ cDNA Systhesis Kit, Clontech). The reaction mix was used as the 1× template standard for PCR in the Lightcycler. Serial dilutions from the 1× template standard were then prepared: $10^{-1}$x, $10^{-2}$x, $10^{31}$ $^3$x, $10^{-4}$x, $10^{-5}$x template standards.

Patient colon tissue was obtained at surgery and stored frozen in liquid nitrogen. The patient tissue samples were homogenized in TRIZOL reagent. Chloroform was then added to isolate RNA, followed by RNA precipitation with isopropanol. The RNA precipitates were washed with 75% ethanol, dried in air, then dissolved in RNase-free distilled water. The total RNA samples were treated with DNase I (RNase-free) (2 U/$\mu$l, Ambion, Austin, Tex.) and cleaned up using RNeasy Mini Kit (Qiagen, Santa Clarita, Calif.) then reverse-transcribed with oligo-dT$_{18}$ primer (1st-Strand™ cDNA Systhesis Kit, Clontech). PCR was performed in the Lightcycler using the following gene-specific primers:

β-actin: forward primer 5'-CGGGAAATCGTGCGTGACATTAAG-3' (SEQ ID NO:16)

reverse primer 5'-TGATCTCCTTCTGCATCCTGTCGG-3' (SEQ ID NO:17)

PCD1: forward primer 5'- TTCGTAGCATCAGTTGAAG-CAGG -3' (SEQ ID NO:18)

reverse primer 5'- GGTGAACCAGCCTTTCCATAGC -3' (SEQ ID NO:19)

The 20-μl PCR reaction mix in each Lightcycler capillary contained 2 μl of 10×PCR buffer II, 3 mM MgCl$_2$ (Perkin-Elmer, Foster City, Calif.), 140 μM dNTP, 1:50000 of SYBR Green I, 0.25 mg/ml BSA, 1 unit of Taq polymerase (Boehringer Mannheim, Indianapolis, Ind.), 0.175 μM each primer, 2 μl of RT reaction mix. The PCR amplification began with 20-second denaturation at 95° C., followed by 45 cycles of denaturation at 95° C. for 5 seconds, annealing at 60° C. for 1 second and extension at 72° C. for 30 seconds. At the end of final cycle, PCR products were annealed at 60° C. for 5 seconds, then slowly heated to 95° C. at 0.2° C./second, to measure melting curves of specific PCR products. All experiments were performed in duplicate. Data analysis was performed using Lightcycler Software (Roche Diagnosis) with quantification and melting curve options.

The quantification assay was based on determination of the cycle crossing point, which represents the cycle when the PCR product begins to double with each cycle, i.e., when the log-linear phase begins. A template dilution test was performed and demonstrated that the gene-specific primers for β-actin and HX2004-6 are capable of accurate, sensitive and specific detection of expression levels for β-actin and HX2004-6, respectively (Data not shown).

For each colon cancer patient, RNA was extracted from a trio of surgical specimens: normal colon tissue, primary colon tumor tissue and metastatic liver tissue from patients with colon cancer. The sample trio from each patient was always tested simultaneously in the same run of the Lightcycler. Each run of the Lightcycler included a standard curve established on β-actin expression in the template standards. β-actin expression in patient tissue samples was used as the internal adjustment control.

The results are quantified and shown in FIGS. 9A–9H. HX2004-6 is overexpressed (>2 fold) in primary tumor colon tissue and/or metastatic liver tissue relative to normal colon tissue in 5/8 patients. Specifically, HX2004-6 was overexpressed in metastatic liver tissue relative to normal tissue in 5/8 patients; HX2004-6 was overexpressed in primary tumor tissue relative to normal tissue in 3/8 patients; and HX2004-6 was overexpressed in either primary tumor and/or metastatic liver tissue relative to normal tissue (i.e., in cancerous tissue relative to normal tissue) in 6/8 patients. These results are consistent with the previous results from in situ hybridization and Northern hybridization described above. It is noteworthy that in one patient, HX2004-6 expression levels in primary tumor colon and metastatic liver tissue are dramatically decreased, not increased, relative to normal colon tissue.

Example 7

Chromosomal Localization of HX2004-6

To determine the chromosomal localization of HX2004-6, the 2004-6 probe was labeled and used as a probe on human metaphase chromosomes using fluorescence in situ hybridization according to standard procedures. The results indicated that HX2004-6 localizes to 13q21.33.

Example 8

Fabricating a DNA Array Using Polynucleotides Differentially Expressed in Ductal Epithelial Cells A DNA array is made by spotting DNA fragments onto glass microscope slides that are pretreated with poly-L-lysine. Spotting onto the array is accomplished by a robotic arrayer. The DNA is cross-linked to the glass by ultraviolet irradiation, and the free poly-L-lysine groups are blocked by treatment with 0.05% succinic anhydride, 50% 1-methyl-2-pyrrolidinone and 50% borate buffer.

The spots on the array are oligonucleotides synthesized on an ABI automated synthesizer. Each spot is one of the polynucleotides of SEQ ID NO:1 or SEQ ID NO:3, a fragment thereof, a complement thereof, or a complement of a fragment thereof, which correspond to a gene that is differentially expressed in pancreatic, breast, or colon epithelial cells according to varying disease states (e.g., overexpressed in cancerous, pancreatic cancer, breast cancer, colorectal cancer cells). The polynucleotides may be present on the array in any of a variety of combinations or subsets. Some internal standards and negative control spots including non-differentially expressed sequences and/or bacterial controls are included.

mRNA from patient samples is isolated, the mRNA used to produce cDNA, amplified and subsequently labeled with fluorescent nucleotides as follows: isolated mRNA is added to a standard PCR reaction containing primers (100 pmoles each), 250 μM nucleotides, and 5 Units of Taq polymerase (Perkin Elmer). In addition, fluorescent nucleotides (Cy3-dUTP (green fluorescence) or Cy5-dUTP (red fluorescence), sold by Amersham) are added to a final concentration of 60 μM. The reaction is carried out in a Perkin Elmer thermocycler (PE9600) for 30 cycles using the following cycle profile: 92° C. for 30 seconds, 58° C. for 30 seconds, and 72° C. for 2 minutes. Unincorporated fluorescent nucleotides are removed by size exclusion chromatography (Microcon-30 concentration devices, sold by Amicon).

Buffer replacement, removal of small nucleotides and primers and sample concentration is accomplished by ultrafiltration over an Amicon microconcentrator-30 (mw cutoff= 30,000 Da) with three changes of 0.45 ml TE. The sample is reduced to 5 μl and supplemented with 1.4 μl 20×SSC and 5 μg yeast tRNA. Particles are removed from this mixture by filtration through a pre-wetted 0.45μ microspin filter (Ultrafree-MC, Millipore, Bedford, Mass.). SDS is added to a 0.28% final concentration. The fluorescently-labeled cDNA mixture is then heated to 98° C. for 2 min., quickly cooled and applied to the DNA array on a microscope slide. Hybridization proceeds under a coverslip, and the slide assembly is kept in a humidified chamber at 65° C. for 15 hours.

The slide is washed briefly in 1×SSC and 0.03% SDS, followed by a wash in 0.06% SSC. The slide is kept in a humidified chamber until fluorescence scanning was done. Fluorescence scanning and data acquisition are then accomplished using any of a variety of suitable methods well known in the art. For example, fluorescence scanning is set for 20 microns/pixel and two readings are taken per pixel. Data for channel 1 is set to collect fluorescence from Cy3 with excitation at 520 nm and emission at 550–600 nm. Channel 2 collects signals excited at 647 nm and emitted at 660–705 nm, appropriate for Cy5. No neutral density filters are applied to the signal from either channel, and the photomultiplier tube gain is set to 5. Fine adjustments are then made to the photomultiplier gain so that signals collected from the two spots are equivalent.

The data acquired from the scan of the array is then converted to any suitable form for analysis. For example, the data may be analyzed using a computer system, and the data may be displayed in a pictoral format on a computer screen, where the display shows the array as a collection of spots, each spot corresponding to a location of a different polynucleotide on the array. The spots vary in brightness according to the amount of fluorescent probe associated with the spot, which in turn is correlated with an amount of hybridized cDNA in the sample. The relative brightness of the spots on the array can be compared with one another to determine their relative intensities, either qualitatively or quantitatively.

The display of spots on the array, along with their relative brightness, provides a test sample pattern. The test sample pattern can be then compared with reference array patterns associated with positive and negative control samples on the same array, e.g., an array having polynucleotides in substantially the same locations as the array used with the test sample. The reference array patterns used in the comparison can be array patterns generated using samples from normal pancreas cells, cancerous pancreatic cells, pancreatitis-associated pancreas cells, normal breast and breast cancer cells, normal colon and colorectal cancer cells, and the like. A substantial or significant match between the test array pattern and a reference array pattern is indicative of a disease state of the patient from whom the test sample was obtained.

The invention now being fully described, it will be apparent to one of ordinary skill in the art that many changes and modifications can be made thereto without departing from the spirit or scope of the appended claims.

What is claimed is:

1. An isolated polynucleotide comprising a sequence selected from the group consisting of:
   (a) a polynucleotide sequence encoding the polypeptide of SEQ ID NO:2;
   (b) a polynucleotide sequence encoding the polypeptide of SEQ ID NO:4;
   (c) a polynucleotide sequence that is a complete complement of the entire length of the polynucleotide sequence of (a); and
   (d) a polynucleotide sequence that is a complete complement of the entire length of the polynucleotide sequence of (b).

2. An isolated polynucleotide of claim 1, wherein said polynucleotide is overexpressed in an adenocarcinoma of a tissue selected from the group consisting of exocrine pancreas, breast, and colon.

3. A recombinant expression vector comprising the isolated polynucleotide of claim 1.

4. An isolated host cell comprising the isolated polynucleotide of claim 1.

5. An in vitro method for producing a polypeptide having an amino acid sequence set forth in SEQ ID NO:2 or SEQ ID NO:4, the method comprising the steps of:
   a) culturing a recombinant host cell containing an isolated polynucleotide of claim 1, wherein said culturing is under conditions suitable for the expression of the polypeptide; and
   b) recovering the polypeptide from the host cell culture.

6. An isolated polynucleotide comprising the polynucleotide sequence of nucleotides 698–1724 of SEQ ID NO:1.

7. The isolated polynucleotide of claim 6, wherein said polynucleotide sequence comprises the polynucleotide sequence of SEQ ID NO:1.

8. The isolated polynucleotide of claim 6, wherein said polynucleotide sequence comprises the polynucleotide sequence of nucleotides 1–1724 of SEQ ID NO:1.

9. An isolated polynucleotide comprising the polynucleotide sequence of SEQ ID NO:1.

10. An isolated polynucleotide comprising the polynucleotide sequence of nucleotides 728–1754 of SEQ ID NO:3.

11. The isolated polynucleotide of claim 10, wherein said isolated polynucleotide sequence comprises the polynucleotide sequence of nucleotides 1–1754 of SEQ ID NO:3.

12. The isolated polynucleotide of claim 10, wherein said polynucleotide sequence comprises the polynucleotide sequence of SEQ ID NO:3.

13. An isolated polynucleotide comprising the polynucleotide sequence of SEQ ID NO:3.

14. An isolated polynucleotide comprising the polynucleotide sequence NO:5.

* * * * *

SEQUENCE LISTING

<160> NUMBER OF SEQ ID NOS: 19

<210> SEQ ID NO 1
<211> LENGTH: 4612
<212> TYPE: DNA
<213> ORGANISM: Homo Sapiens
<220> FEATURE:
<221> NAME/KEY: CDS
<222> LOCATION: (698)...(3862)

<400> SEQUENCE: 1

```
atagcacgac tgtgtatgct ctggaggact gaaaggctgt acaagcccta tgtattttt       60 ttcaaatata catatgcatg ggtcttgctg ctgcctcttt tgctgactgt aattggactt     120
tgaagcttcg aagttatatc ataaaaattt gtaacctttg tctgagagag agctcagcta     180
agcaatcact ttccacttct tttcacagga taatataaac gttttcttga aagcttgtga     240
acagattgga ttgaaagaag cccagctttt ccatcctgga gatctacagg atttatcaaa     300
tcgagtcact gtcaagcaag aagagactga caggagagtg aaaaatgttt tgataacatt     360
gtactggctg ggaagaaaag cacaaagcaa cccgtactat aatggtcccc atcttaattt     420
gaaagcgttt gagaatcttt taggacaagc actgacgaag gcactcgaag actccagctt     480
cctgaaaaga agtggcaggg acagtggcta cggtgacatc tggtgtcctg aacgtggaga     540
atttcttgct cctccaaggc accataagag agaagattcc tttgaaagct tggactcttt     600
gggctcgagg tcattgacaa gctgctcctc tgatatcacg ttgagagggg ggcgtgaagg     660
ttttgaaagt gacacagatt cggaatttac attcaag atg cag gat tat aat aaa     715
                                         Met Gln Asp Tyr Asn Lys
                                         1               5
```

```
gat gat atg tcg tat cga agg att tcg gct gtt gag cca aag act gcg    763
Asp Asp Met Ser Tyr Arg Arg Ile Ser Ala Val Glu Pro Lys Thr Ala
            10                  15                  20 tta ccc ttc aat cgt ttt tta ccc aac aaa agt aga cag cca tcc tat    811
Leu Pro Phe Asn Arg Phe Leu Pro Asn Lys Ser Arg Gln Pro Ser Tyr
        25                  30                  35 gta cca gca cct ctg aga aag aaa aag cca gac aaa cat gag gat aac    859
Val Pro Ala Pro Leu Arg Lys Lys Lys Pro Asp Lys His Glu Asp Asn
    40                  45                  50 aga aga agt tgg gca agc ccg gtt tat aca gaa gca gat gga aca ttt    907
Arg Arg Ser Trp Ala Ser Pro Val Tyr Thr Glu Ala Asp Gly Thr Phe
55                  60                  65                  70 tca agg agt aag tcc atg agt gat gtc agc gca gaa gat gtt caa aac    955
Ser Arg Ser Lys Ser Met Ser Asp Val Ser Ala Glu Asp Val Gln Asn
                75                  80                  85 ttg cgt cag ctg cgt tac gag gag atg cag aaa ata aaa tca caa tta   1003
Leu Arg Gln Leu Arg Tyr Glu Glu Met Gln Lys Ile Lys Ser Gln Leu
```

```
                    90                      95                     100
aaa gaa caa gat cag aaa tgg cag gat gac ctt gca aaa tgg aaa gat         1051
Lys Glu Gln Asp Gln Lys Trp Gln Asp Asp Leu Ala Lys Trp Lys Asp
                105                     110                 115 cgt cga aaa agt tac act tca gat ctg cag aag aaa aaa gaa gag aga         1099
Arg Arg Lys Ser Tyr Thr Ser Asp Leu Gln Lys Lys Lys Glu Glu Arg
        120                     125                 130 gaa gaa att gaa aag cag gca ctt gag aag tct aag aga agc tct aag         1147
Glu Glu Ile Glu Lys Gln Ala Leu Glu Lys Ser Lys Arg Ser Ser Lys
135                     140                 145                 150 acg ttt aag gaa atg ctg cag gac agg gaa tcc caa aat caa aag tct         1195
Thr Phe Lys Glu Met Leu Gln Asp Arg Glu Ser Gln Asn Gln Lys Ser
                    155                 160                 165 aca gtt ccg tca aga agg aga atg tat tct ttt gat gat gtg ctg gag         1243
Thr Val Pro Ser Arg Arg Arg Met Tyr Ser Phe Asp Asp Val Leu Glu
                170                 175                 180 gaa gga aag cga ccc cct aca atg act gtg tca gaa gca agt tac cag         1291
Glu Gly Lys Arg Pro Pro Thr Met Thr Val Ser Glu Ala Ser Tyr Gln
            185                 190                 195 agt gag aga gta gaa gag aag gga gca act tat cct tca gaa att ccc         1339
Ser Glu Arg Val Glu Glu Lys Gly Ala Thr Tyr Pro Ser Glu Ile Pro
    200                 205                 210 aaa gaa gat tct acc act ttt gca aaa aga gag gac cgt gta aca act         1387
Lys Glu Asp Ser Thr Thr Phe Ala Lys Arg Glu Asp Arg Val Thr Thr
215                 220                 225                 230 gaa att cag ctt cct tct caa agt cct gtg gaa gaa caa agc cca gcc         1435
Glu Ile Gln Leu Pro Ser Gln Ser Pro Val Glu Glu Gln Ser Pro Ala
                235                 240                 245 tct ttg tct tct ctg cgt tca cgg agc aca caa atg gaa tca act cgt         1483
Ser Leu Ser Ser Leu Arg Ser Arg Ser Thr Gln Met Glu Ser Thr Arg
            250                 255                 260 gtt tca gct tct ctc ccc aga agt tac cgg aaa act gat aca gtc agg         1531
Val Ser Ala Ser Leu Pro Arg Ser Tyr Arg Lys Thr Asp Thr Val Arg
        265                 270                 275 tta aca tct gtg gtc aca cca aga ccc ttt ggc tct cag aca agg gga         1579
Leu Thr Ser Val Val Thr Pro Arg Pro Phe Gly Ser Gln Thr Arg Gly
    280                 285                 290 atc tca tca ctc ccc aga tct tac acg atg gat gat gct tgg aag tat         1627
Ile Ser Ser Leu Pro Arg Ser Tyr Thr Met Asp Asp Ala Trp Lys Tyr
295                 300                 305                 310 aat gga gat gtt gaa gac att aag aga act cca aac aat gtg gtc agc         1675
Asn Gly Asp Val Glu Asp Ile Lys Arg Thr Pro Asn Asn Val Val Ser
                315                 320                 325 acc cct gca cca agc ccg gac gca agc caa ctg gct tca agc tta tct         1723
Thr Pro Ala Pro Ser Pro Asp Ala Ser Gln Leu Ala Ser Ser Leu Ser
            330                 335                 340 agc cag aaa gag gta gca gca aca gaa gaa gat gtg aca agg ctg ccc         1771
Ser Gln Lys Glu Val Ala Ala Thr Glu Glu Asp Val Thr Arg Leu Pro
        345                 350                 355 tct cct aca tcc ccc ttc tca tct ctt tcc caa gac cag gct gcc act         1819
Ser Pro Thr Ser Pro Phe Ser Ser Leu Ser Gln Asp Gln Ala Ala Thr
    360                 365                 370 tct aaa gcc aca ttg tct tcc aca tct ggt ctt gat tta atg tct gaa         1867
Ser Lys Ala Thr Leu Ser Ser Thr Ser Gly Leu Asp Leu Met Ser Glu
375                 380                 385                 390 tct gga gaa ggg gaa atc tcc cca caa aga gaa gtc tca aga tcc cag         1915
Ser Gly Glu Gly Glu Ile Ser Pro Gln Arg Glu Val Ser Arg Ser Gln
                395                 400                 405 gat cag ttc agt gat atg aga atc agc ata aac cag acg cct ggg aag         1963
```

```
Asp Gln Phe Ser Asp Met Arg Ile Ser Ile Asn Gln Thr Pro Gly Lys
            410                 415                 420 agt ctt gac ttt ggg ttt aca ata aaa tgg gat att cct ggg atc ttc       2011
Ser Leu Asp Phe Gly Phe Thr Ile Lys Trp Asp Ile Pro Gly Ile Phe
        425                 430                 435 gta gca tca gtt gaa gca ggt agc cca gca gaa ttt tct cag cta caa       2059
Val Ala Ser Val Glu Ala Gly Ser Pro Ala Glu Phe Ser Gln Leu Gln
        440                 445                 450 gta gat gat gaa att att gct att aac aac acc aag ttt tca tat aac       2107
Val Asp Asp Glu Ile Ile Ala Ile Asn Asn Thr Lys Phe Ser Tyr Asn
455                 460                 465                 470 gat tca aaa gag tgg gag gaa gcc atg gct aag gct caa gaa act gga       2155
Asp Ser Lys Glu Trp Glu Glu Ala Met Ala Lys Ala Gln Glu Thr Gly
                475                 480                 485 cac cta gtg atg gat gtg agg cgc tat gga aag gct ggt tca cct gaa       2203
His Leu Val Met Asp Val Arg Arg Tyr Gly Lys Ala Gly Ser Pro Glu
            490                 495                 500 aca aag tgg att gat gca act tct gga att tac aac tca gaa aaa tct       2251
Thr Lys Trp Ile Asp Ala Thr Ser Gly Ile Tyr Asn Ser Glu Lys Ser
        505                 510                 515 tca aat cta tct gta aca act gat ttc tcc gaa agc ctt cag agt tct       2299
Ser Asn Leu Ser Val Thr Thr Asp Phe Ser Glu Ser Leu Gln Ser Ser
        520                 525                 530 aat att gaa tcc aaa gaa atc aat gga att cat gat gaa agc aat gct       2347
Asn Ile Glu Ser Lys Glu Ile Asn Gly Ile His Asp Glu Ser Asn Ala
535                 540                 545                 550 ttt gaa tca aaa gca tct gaa tcc att tct ttg aaa aac tta aaa agg       2395
Phe Glu Ser Lys Ala Ser Glu Ser Ile Ser Leu Lys Asn Leu Lys Arg
                555                 560                 565 cga tca caa ttt ttt gaa caa gga agc tct gat tcg gtg gtt cct gat       2443
Arg Ser Gln Phe Phe Glu Gln Gly Ser Ser Asp Ser Val Val Pro Asp
            570                 575                 580 ctt cca gtt cca acc atc agt gcc ccg agt cgc tgg gtg tgg gat caa       2491
Leu Pro Val Pro Thr Ile Ser Ala Pro Ser Arg Trp Val Trp Asp Gln
        585                 590                 595 gag gag gag cgg aag cgg cag gag agg tgg cag aag gag cag gac cgc       2539
Glu Glu Glu Arg Lys Arg Gln Glu Arg Trp Gln Lys Glu Gln Asp Arg
        600                 605                 610 cta ctg cag gaa aaa tat caa cgt gag cag gag aaa ctg agg gaa gag       2587
Leu Leu Gln Glu Lys Tyr Gln Arg Glu Gln Glu Lys Leu Arg Glu Glu
615                 620                 625                 630 tgg caa agg gcc aaa cag gag gca gag aga gag aat tcc aag tac ttg       2635
Trp Gln Arg Ala Lys Gln Glu Ala Glu Arg Glu Asn Ser Lys Tyr Leu
                635                 640                 645 gat gag gaa ctg atg gtc cta agc tca aac agc atg tct ctg acc aca       2683
Asp Glu Glu Leu Met Val Leu Ser Ser Asn Ser Met Ser Leu Thr Thr
            650                 655                 660 cgg gag ccc tct ctt gcc acc tgg gaa gct acc tgg agt gaa ggg tcc       2731
Arg Glu Pro Ser Leu Ala Thr Trp Glu Ala Thr Trp Ser Glu Gly Ser
        665                 670                 675 aag tct tca gac aga gaa gga acc cga gca gga gaa gag gag agg aga       2779
Lys Ser Ser Asp Arg Glu Gly Thr Arg Ala Gly Glu Glu Glu Arg Arg
        680                 685                 690 cag cca caa gag gaa gtt gtt cat gag gac caa gga aag aag ccg cag       2827
Gln Pro Gln Glu Glu Val Val His Glu Asp Gln Gly Lys Lys Pro Gln
695                 700                 705                 710 gat cag ctt gtt att gag aga gag agg aaa tgg gag caa cag ctt cag       2875
Asp Gln Leu Val Ile Glu Arg Glu Arg Lys Trp Glu Gln Gln Leu Gln
                715                 720                 725
```

-continued

| | | |
|---|---|---|
| gaa gag caa gag caa aag cgg ctt cag gct gag gct gag gag cag aag<br>Glu Glu Gln Glu Gln Lys Arg Leu Gln Ala Glu Ala Glu Glu Gln Lys<br>730               735               740 | | 2923 |
| cgt cct gcg gag gag cag aag cgc cag gca gag ata gag cgg gaa aca<br>Arg Pro Ala Glu Glu Gln Lys Arg Gln Ala Glu Ile Glu Arg Glu Thr<br>     745              750               755 | | 2971 |
| tca gtc aga ata tac cag tac agg agg cct gtt gat tcc tat gat ata<br>Ser Val Arg Ile Tyr Gln Tyr Arg Arg Pro Val Asp Ser Tyr Asp Ile<br>760               765               770 | | 3019 |
| cca aag aca gaa gaa gca tct tca ggt ttt ctt cct ggt gac agg aat<br>Pro Lys Thr Glu Glu Ala Ser Ser Gly Phe Leu Pro Gly Asp Arg Asn<br>775               780              785               790 | | 3067 |
| aaa tcc aga tct act act gaa ctg gat gat tac tcc aca aat aaa aat<br>Lys Ser Arg Ser Thr Thr Glu Leu Asp Asp Tyr Ser Thr Asn Lys Asn<br>               795              800               805 | | 3115 |
| gga aac aat aaa tat tta gac caa att ggg aac acg acc tct tca cag<br>Gly Asn Asn Lys Tyr Leu Asp Gln Ile Gly Asn Thr Thr Ser Ser Gln<br>810               815               820 | | 3163 |
| agg aga tcc aag aaa gaa caa gta cca tca gga gca gaa ttg gag agg<br>Arg Arg Ser Lys Lys Glu Gln Val Pro Ser Gly Ala Glu Leu Glu Arg<br>825               830              835 | | 3211 |
| caa caa atc ctt cag gaa atg agg aag aga aca ccc ctt cac aat gac<br>Gln Gln Ile Leu Gln Glu Met Arg Lys Arg Thr Pro Leu His Asn Asp<br>840               845              850 | | 3259 |
| aac agc tgg atc cga cag cgc agt gcc agt gtc aac aaa gag cct gtt<br>Asn Ser Trp Ile Arg Gln Arg Ser Ala Ser Val Asn Lys Glu Pro Val<br>855               860              865               870 | | 3307 |
| agt ctt cct ggg atc atg aga aga ggc gaa tct tta gat aac ctg gac<br>Ser Leu Pro Gly Ile Met Arg Arg Gly Glu Ser Leu Asp Asn Leu Asp<br>               875              880               885 | | 3355 |
| tcc ccc cga tcc aat tct tgg aga cag cct cct tgg ctc aat cag ccc<br>Ser Pro Arg Ser Asn Ser Trp Arg Gln Pro Pro Trp Leu Asn Gln Pro<br>890               895              900 | | 3403 |
| aca gga ttc tat gct tct tcc tct gtg caa gac ttt agt cgc cca cca<br>Thr Gly Phe Tyr Ala Ser Ser Ser Val Gln Asp Phe Ser Arg Pro Pro<br>     905              910               915 | | 3451 |
| cct cag ctg gtg tcc aca tca aac cgt gcc tac atg cgg aac ccc tcc<br>Pro Gln Leu Val Ser Thr Ser Asn Arg Ala Tyr Met Arg Asn Pro Ser<br>920               925              930 | | 3499 |
| tcc agc gtg ccc cca cct tca gct ggc tcc gtg aag acc tcc acc aca<br>Ser Ser Val Pro Pro Pro Ser Ala Gly Ser Val Lys Thr Ser Thr Thr<br>935               940              945               950 | | 3547 |
| ggt gtg gcc acc aca cag tcc ccc acc ccg aga agc cat tcc cct tca<br>Gly Val Ala Thr Thr Gln Ser Pro Thr Pro Arg Ser His Ser Pro Ser<br>               955              960               965 | | 3595 |
| gct tca cag tca ggc tct cag ctg cgt aac agg tca gtc agt ggg aag<br>Ala Ser Gln Ser Gly Ser Gln Leu Arg Asn Arg Ser Val Ser Gly Lys<br>970               975              980 | | 3643 |
| cgc ata tgc tcc tac tgc aat aac att ctg ggc aaa gga gcc gcc atg<br>Arg Ile Cys Ser Tyr Cys Asn Asn Ile Leu Gly Lys Gly Ala Ala Met<br>     985              990               995 | | 3691 |
| atc atc gag tcc ctg ggt ctt tgt tat cat ttg cat tgt ttt aag tgt<br>Ile Ile Glu Ser Leu Gly Leu Cys Tyr His Leu His Cys Phe Lys Cys<br>1000              1005              1010 | | 3739 |
| gtt gcc tgt gag tgt gac ctc gga ggc tct tca gga gct gaa gtc<br>Val Ala Cys Glu Cys Asp Leu Gly Gly Ser Ser Gly Ala Glu Val<br>1015              1020              1025              1030 | | 3787 |
| agg atc aga aac cac caa ctg tac tgc aac gac tgc tat ctc aga ttc<br>Arg Ile Arg Asn His Gln Leu Tyr Cys Asn Asp Cys Tyr Leu Arg Phe<br>               1035              1040              1045 | | 3835 |

-continued

```
aaa tct gga cgg cca acc gcc atg tga tgtaagcctc catacgaaag     3882
Lys Ser Gly Arg Pro Thr Ala Met  *
             1050 cactgttgca gatagaagaa gaggtggttg ctgctcatgt agatctataa atatgtgttg    3942 tatgtctttt ttgctttttt tttaaaaaaa agaataactt ttttttgcctc tttagattac    4002 atagaagcat tgtagtcttg gtagaaccag tatttttgtt gtttatttat aaggtaattg    4062 tgtgtggga aaagtgcagt atttacctgt tgaattcagc atcttgagag cacaagggaa    4122 aaaataagaa cctacgaata tttttgaggc agataatgat ctagtttgac tttctagtta    4182 gtggtgtttt gaagagggta ttttattgtt ttttaaaaaa aggttcttaa acattatttg    4242 aaatagttaa tataaataca taattgcatt tgctctgttt attgtaatgt attctaaatt    4302 aatgcagaac catatggaaa atttcattaa aatctatccc caaatgtgct ttctgtatcc    4362 ttccttctac ctattattct gattttttaaa aatgcagtta atgtaccatt tatttgcttg    4422 atgaagggag ctctattttc tttaccagaa atgttgctaa gtaattccca atagaaagct    4482 gcttattttc attaatgaaa aataaccatg gtttgtatac tagaagtctt cttcagaaac    4542 tggtgagcct ttctgttcaa ttgcatttgt aaataaactt gctgatgcat ttaaaaaaaa    4602 aaaaaaaaaa                                                           4612
```

<210> SEQ ID NO 2
<211> LENGTH: 1054
<212> TYPE: PRT
<213> ORGANISM: Homo Sapiens

<400> SEQUENCE: 2

```
Met Gln Asp Tyr Asn Lys Asp Asp Met Ser Tyr Arg Arg Ile Ser Ala
 1               5                  10                  15

Val Glu Pro Lys Thr Ala Leu Pro Phe Asn Arg Phe Leu Pro Asn Lys
             20                  25                  30

Ser Arg Gln Pro Ser Tyr Val Pro Ala Pro Leu Arg Lys Lys Lys Pro
         35                  40                  45

Asp Lys His Glu Asp Asn Arg Arg Ser Trp Ala Ser Pro Val Tyr Thr
     50                  55                  60

Glu Ala Asp Gly Thr Phe Ser Arg Ser Lys Ser Met Ser Asp Val Ser
 65                  70                  75                  80

Ala Glu Asp Val Gln Asn Leu Arg Gln Leu Arg Tyr Glu Glu Met Gln
                 85                  90                  95

Lys Ile Lys Ser Gln Leu Lys Glu Gln Asp Gln Lys Trp Gln Asp Asp
            100                 105                 110

Leu Ala Lys Trp Lys Asp Arg Arg Lys Ser Tyr Thr Ser Asp Leu Gln
        115                 120                 125

Lys Lys Lys Glu Glu Arg Glu Ile Glu Lys Gln Ala Leu Glu Lys
    130                 135                 140

Ser Lys Arg Ser Ser Lys Thr Phe Lys Glu Met Leu Gln Asp Arg Glu
145                 150                 155                 160

Ser Gln Asn Gln Lys Ser Thr Val Pro Ser Arg Arg Met Tyr Ser
                165                 170                 175

Phe Asp Asp Val Leu Glu Glu Gly Lys Arg Pro Pro Thr Met Thr Val
            180                 185                 190

Ser Glu Ala Ser Tyr Gln Ser Glu Arg Val Glu Glu Lys Gly Ala Thr
        195                 200                 205

Tyr Pro Ser Glu Ile Pro Lys Glu Asp Ser Thr Thr Phe Ala Lys Arg
```

-continued

```
            210                 215                 220
Glu Asp Arg Val Thr Thr Glu Ile Gln Leu Pro Ser Gln Ser Pro Val
225                 230                 235                 240

Glu Glu Gln Ser Pro Ala Ser Leu Ser Ser Leu Arg Ser Arg Ser Thr
                245                 250                 255

Gln Met Glu Ser Thr Arg Val Ser Ala Ser Leu Pro Arg Ser Tyr Arg
                260                 265                 270

Lys Thr Asp Thr Val Arg Leu Thr Ser Val Val Thr Pro Arg Pro Phe
                275                 280                 285

Gly Ser Gln Thr Arg Gly Ile Ser Ser Leu Pro Arg Ser Tyr Thr Met
                290                 295                 300

Asp Asp Ala Trp Lys Tyr Asn Gly Asp Val Glu Asp Ile Lys Arg Thr
305                 310                 315                 320

Pro Asn Asn Val Val Ser Thr Pro Ala Pro Ser Pro Asp Ala Ser Gln
                325                 330                 335

Leu Ala Ser Ser Leu Ser Ser Gln Lys Glu Val Ala Ala Thr Glu Glu
                340                 345                 350

Asp Val Thr Arg Leu Pro Ser Pro Thr Ser Pro Phe Ser Ser Leu Ser
                355                 360                 365

Gln Asp Gln Ala Ala Thr Ser Lys Ala Thr Leu Ser Ser Thr Ser Gly
370                 375                 380

Leu Asp Leu Met Ser Glu Ser Gly Glu Gly Glu Ile Ser Pro Gln Arg
385                 390                 395                 400

Glu Val Ser Arg Ser Gln Asp Gln Phe Ser Asp Met Arg Ile Ser Ile
                405                 410                 415

Asn Gln Thr Pro Gly Lys Ser Leu Asp Phe Gly Phe Thr Ile Lys Trp
                420                 425                 430

Asp Ile Pro Gly Ile Phe Val Ala Ser Val Glu Ala Gly Ser Pro Ala
                435                 440                 445

Glu Phe Ser Gln Leu Gln Val Asp Asp Glu Ile Ile Ala Ile Asn Asn
                450                 455                 460

Thr Lys Phe Ser Tyr Asn Asp Ser Lys Glu Trp Glu Glu Ala Met Ala
465                 470                 475                 480

Lys Ala Gln Glu Thr Gly His Leu Val Met Asp Val Arg Arg Tyr Gly
                485                 490                 495

Lys Ala Gly Ser Pro Glu Thr Lys Trp Ile Asp Ala Thr Ser Gly Ile
                500                 505                 510

Tyr Asn Ser Glu Lys Ser Ser Asn Leu Ser Val Thr Thr Asp Phe Ser
                515                 520                 525

Glu Ser Leu Gln Ser Ser Asn Ile Glu Ser Lys Glu Ile Asn Gly Ile
                530                 535                 540

His Asp Glu Ser Asn Ala Phe Glu Ser Lys Ala Ser Glu Ser Ile Ser
545                 550                 555                 560

Leu Lys Asn Leu Lys Arg Arg Ser Gln Phe Phe Glu Gln Gly Ser Ser
                565                 570                 575

Asp Ser Val Val Pro Asp Leu Pro Val Pro Thr Ile Ser Ala Pro Ser
                580                 585                 590

Arg Trp Val Trp Asp Gln Glu Glu Glu Arg Lys Arg Gln Glu Arg Trp
                595                 600                 605

Gln Lys Glu Gln Asp Arg Leu Leu Gln Glu Lys Tyr Gln Arg Glu Gln
                610                 615                 620

Glu Lys Leu Arg Glu Glu Trp Gln Arg Ala Lys Gln Glu Ala Glu Arg
625                 630                 635                 640
```

```
                                     -continued

Glu Asn Ser Lys Tyr Leu Asp Glu Glu Leu Met Val Leu Ser Ser Asn
                645                 650                 655

Ser Met Ser Leu Thr Thr Arg Glu Pro Ser Leu Ala Thr Trp Glu Ala
            660                 665                 670

Thr Trp Ser Glu Gly Ser Lys Ser Ser Asp Arg Glu Gly Thr Arg Ala
            675                 680                 685

Gly Glu Glu Arg Arg Gln Pro Gln Glu Val His Glu Asp
            690                 695                 700

Gln Gly Lys Lys Pro Gln Asp Gln Leu Val Ile Glu Arg Glu Arg Lys
705                 710                 715                 720

Trp Glu Gln Gln Leu Gln Glu Glu Gln Glu Lys Arg Leu Gln Ala
                725                 730                 735

Glu Ala Glu Glu Gln Lys Arg Pro Ala Glu Glu Gln Lys Arg Gln Ala
            740                 745                 750

Glu Ile Glu Arg Glu Thr Ser Val Arg Ile Tyr Gln Tyr Arg Arg Pro
            755                 760                 765

Val Asp Ser Tyr Asp Ile Pro Lys Thr Glu Ala Ser Ser Gly Phe
770                 775                 780

Leu Pro Gly Asp Arg Asn Lys Ser Arg Ser Thr Thr Glu Leu Asp Asp
785                 790                 795                 800

Tyr Ser Thr Asn Lys Asn Gly Asn Asn Lys Tyr Leu Asp Gln Ile Gly
                805                 810                 815

Asn Thr Thr Ser Ser Gln Arg Arg Ser Lys Lys Glu Gln Val Pro Ser
            820                 825                 830

Gly Ala Glu Leu Glu Arg Gln Gln Ile Leu Gln Glu Met Arg Lys Arg
            835                 840                 845

Thr Pro Leu His Asn Asp Asn Ser Trp Ile Arg Gln Arg Ser Ala Ser
850                 855                 860

Val Asn Lys Glu Pro Val Ser Leu Pro Gly Ile Met Arg Arg Gly Glu
865                 870                 875                 880

Ser Leu Asp Asn Leu Asp Ser Pro Arg Ser Asn Ser Trp Arg Gln Pro
                885                 890                 895

Pro Trp Leu Asn Gln Pro Thr Gly Phe Tyr Ala Ser Ser Ser Val Gln
                900                 905                 910

Asp Phe Ser Arg Pro Pro Gln Leu Val Ser Thr Ser Asn Arg Ala
            915                 920                 925

Tyr Met Arg Asn Pro Ser Ser Val Pro Pro Ser Ala Gly Ser
            930                 935                 940

Val Lys Thr Ser Thr Thr Gly Val Ala Thr Thr Gln Ser Pro Thr Pro
945                 950                 955                 960

Arg Ser His Ser Pro Ser Ala Ser Gln Ser Gly Ser Gln Leu Arg Asn
                965                 970                 975

Arg Ser Val Ser Gly Lys Arg Ile Cys Ser Tyr Cys Asn Asn Ile Leu
            980                 985                 990

Gly Lys Gly Ala Ala Met Ile Ile Glu Ser Leu Gly Leu Cys Tyr His
            995                 1000                1005

Leu His Cys Phe Lys Cys Val Ala Cys Glu Cys Asp Leu Gly Gly Ser
    1010                1015                1020

Ser Ser Gly Ala Glu Val Arg Ile Arg Asn His Gln Leu Tyr Cys Asn
1025                1030                1035                1040

Asp Cys Tyr Leu Arg Phe Lys Ser Gly Arg Pro Thr Ala Met
                1045                1050
```

```
<210> SEQ ID NO 3
<211> LENGTH: 4642
<212> TYPE: DNA
<213> ORGANISM: Homo Sapiens
<220> FEATURE:
<221> NAME/KEY: CDS
<222> LOCATION: (698)...(3892)

<400> SEQUENCE: 3
atagcacgac tgtgtatgct ctggaggact gaaaggctgt acaagcccta tgtattttt      60 ttcaaatata catatgcatg ggtcttgctg ctgcctcttt tgctgactgt aattggactt   120
tgaagcttcg aagttatatc ataaaaattt gtaacctttg tctgagagag agctcagcta   180
agcaatcact ttccacttct tttcacagga taatataaac gttttcttga aagcttgtga   240
acagattgga ttgaaagaag cccagctttt ccatcctgga gatctacagg atttatcaaa   300
tcgagtcact gtcaagcaag aagagactga caggagagtg aaaaatgttt tgataacatt   360
gtactggctg ggaagaaaag cacaaagcaa cccgtactat aatggtcccc atcttaattt   420
gaaagcgttt gagaatcttt taggacaagc actgacgaag gcactcgaag actccagctt   480
cctgaaaaga agtggcaggg acagtggcta cggtgacatc tggtgtcctg aacgtggaga   540
atttcttgct cctccaaggc accataagag agaagattcc tttgaaagct tggactcttt   600
gggctcgagg tcattgacaa gctgctcctc tgatatcacg ttgagagggg ggcgtgaagg   660
ttttgaaagt gacacagatt cggaatttac attcaag atg cag gat tat aat aaa   715
                                       Met Gln Asp Tyr Asn Lys
                                         1               5 gat gat atg tcg tat cga agg att tcg gct gtt gag cca aag act gcg   763
Asp Asp Met Ser Tyr Arg Arg Ile Ser Ala Val Glu Pro Lys Thr Ala
            10                  15                  20 tta ccc ttc aat cgt ttt tta ccc aac aaa agt aga cag cca tcc tat   811
Leu Pro Phe Asn Arg Phe Leu Pro Asn Lys Ser Arg Gln Pro Ser Tyr
        25                  30                  35 gta cca gca cct ctg aga aag aaa aag cca gac aaa cat gag gat aac   859
Val Pro Ala Pro Leu Arg Lys Lys Lys Pro Asp Lys His Glu Asp Asn
    40                  45                  50 aga aga agt tgg gca agc ccg gtt tat aca gaa gca gat gga aca ttt   907
Arg Arg Ser Trp Ala Ser Pro Val Tyr Thr Glu Ala Asp Gly Thr Phe
55                  60                  65                  70 tca aga ctc ttt caa aag att tat ggt gag aat ggg agt aag tcc atg   955
Ser Arg Leu Phe Gln Lys Ile Tyr Gly Glu Asn Gly Ser Lys Ser Met
                75                  80                  85 agt gat gtc agc gca gaa gat gtt caa aac ttg cgt cag ctg cgt tac   1003
Ser Asp Val Ser Ala Glu Asp Val Gln Asn Leu Arg Gln Leu Arg Tyr
            90                  95                 100 gag gag atg cag aaa ata aaa tca caa tta aaa gaa caa gat cag aaa   1051
Glu Glu Met Gln Lys Ile Lys Ser Gln Leu Lys Glu Gln Asp Gln Lys
        105                 110                 115 tgg cag gat gac ctt gca aaa tgg aaa gat cgt cga aaa agt tac act   1099
Trp Gln Asp Asp Leu Ala Lys Trp Lys Asp Arg Arg Lys Ser Tyr Thr
    120                 125                 130 tca gat ctg cag aag aaa aaa gaa gag aga gaa gaa att gaa aag cag   1147
Ser Asp Leu Gln Lys Lys Lys Glu Glu Arg Glu Glu Ile Glu Lys Gln
135                 140                 145                 150 gca ctt gag aag tct aag aga agc tct aag acg ttt aag gaa atg ctg   1195
Ala Leu Glu Lys Ser Lys Arg Ser Ser Lys Thr Phe Lys Glu Met Leu
                155                 160                 165 cag gac agg gaa tcc caa aat caa aag tct aca gtt ccg tca aga agg   1243
Gln Asp Arg Glu Ser Gln Asn Gln Lys Ser Thr Val Pro Ser Arg Arg
```

```
                    170                 175                 180
aga atg tat tct ttt gat gat gtg ctg gag gaa gga aag cga ccc cct     1291
Arg Met Tyr Ser Phe Asp Asp Val Leu Glu Glu Gly Lys Arg Pro Pro
            185                 190                 195 aca atg act gtg tca gaa gca agt tac cag agt gag aga gta gaa gag     1339
Thr Met Thr Val Ser Glu Ala Ser Tyr Gln Ser Glu Arg Val Glu Glu
    200                 205                 210 aag gga gca act tat cct tca gaa att ccc aaa gaa gat tct acc act     1387
Lys Gly Ala Thr Tyr Pro Ser Glu Ile Pro Lys Glu Asp Ser Thr Thr
215                 220                 225                 230 ttt gca aaa aga gag gac cgt gta aca act gaa att cag ctt cct tct     1435
Phe Ala Lys Arg Glu Asp Arg Val Thr Thr Glu Ile Gln Leu Pro Ser
                235                 240                 245 caa agt cct gtg gaa gaa caa agc cca gcc tct ttg tct tct ctg cgt     1483
Gln Ser Pro Val Glu Glu Gln Ser Pro Ala Ser Leu Ser Ser Leu Arg
            250                 255                 260 tca cgg agc aca caa atg gaa tca act cgt gtt tca gct tct ctc ccc     1531
Ser Arg Ser Thr Gln Met Glu Ser Thr Arg Val Ser Ala Ser Leu Pro
        265                 270                 275 agt agt tac cgg aaa act gat aca gtc agg tta aca tct gtg gtc aca     1579
Arg Ser Tyr Arg Lys Thr Asp Thr Val Arg Leu Thr Ser Val Val Thr
280                 285                 290 cca aga ccc ttt ggc tct cag aca agg gga atc tca tca ctc ccc aga     1627
Pro Arg Pro Phe Gly Ser Gln Thr Arg Gly Ile Ser Ser Leu Pro Arg
295                 300                 305                 310 tct tac acg atg gat gat gct tgg aag tat aat gga gat gtt gaa gac     1675
Ser Tyr Thr Met Asp Asp Ala Trp Lys Tyr Asn Gly Asp Val Glu Asp
                315                 320                 325 att aag aga act cca aac aat gtg gtc agc acc cct gca cca agc ccg     1723
Ile Lys Arg Thr Pro Asn Asn Val Val Ser Thr Pro Ala Pro Ser Pro
            330                 335                 340 gac gca agc caa ctg gct tca agc tta tct agc cag aaa gag gta gca     1771
Asp Ala Ser Gln Leu Ala Ser Ser Leu Ser Ser Gln Lys Glu Val Ala
        345                 350                 355 gca aca gaa gaa gat gtg aca agg ctg ccc tct cct aca tcc ccc ttc     1819
Ala Thr Glu Glu Asp Val Thr Arg Leu Pro Ser Pro Thr Ser Pro Phe
    360                 365                 370 tca tct ctt tcc caa gac cag gct gcc act tct aaa gcc aca ttg tct     1867
Ser Ser Leu Ser Gln Asp Gln Ala Ala Thr Ser Lys Ala Thr Leu Ser
375                 380                 385                 390 tcc aca tct ggt ctt gat tta atg tct gaa tct gga gaa ggg gaa atc     1915
Ser Thr Ser Gly Leu Asp Leu Met Ser Glu Ser Gly Glu Gly Glu Ile
                395                 400                 405 tcc cca caa aga gaa gtc tca aga tcc cag gat cag ttc agt gat atg     1963
Ser Pro Gln Arg Glu Val Ser Arg Ser Gln Asp Gln Phe Ser Asp Met
            410                 415                 420 aga atc agc ata aac cag acg cct ggg aag agt ctt gac ttt ggg ttt     2011
Arg Ile Ser Ile Asn Gln Thr Pro Gly Lys Ser Leu Asp Phe Gly Phe
        425                 430                 435 aca ata aaa tgg gat att cct ggg atc ttc gta gca tca gtt gaa gca     2059
Thr Ile Lys Trp Asp Ile Pro Gly Ile Phe Val Ala Ser Val Glu Ala
    440                 445                 450 ggt agc cca gca gaa ttt tct cag cta caa gta gat gat gaa att att     2107
Gly Ser Pro Ala Glu Phe Ser Gln Leu Gln Val Asp Asp Glu Ile Ile
455                 460                 465                 470 gct att aac aac acc aag ttt tca tat aac gat tca aaa gag tgg gag     2155
Ala Ile Asn Asn Thr Lys Phe Ser Tyr Asn Asp Ser Lys Glu Trp Glu
                475                 480                 485 gaa gcc atg gct aag gct caa gaa act gga cac cta gtg atg gat gtg     2203
```

-continued

```
                Glu Ala Met Ala Lys Ala Gln Glu Thr Gly His Leu Val Met Asp Val
                                490                 495                 500 agg cgc tat gga aag gct ggt tca cct gaa aca aag tgg att gat gca      2251
Arg Arg Tyr Gly Lys Ala Gly Ser Pro Glu Thr Lys Trp Ile Asp Ala
            505                 510                 515 act tct gga att tac aac tca gaa aaa tct tca aat cta tct gta aca      2299
Thr Ser Gly Ile Tyr Asn Ser Glu Lys Ser Ser Asn Leu Ser Val Thr
    520                 525                 530 act gat ttc tcc gaa agc ctt cag agt tct aat att gaa tcc aaa gaa      2347
Thr Asp Phe Ser Glu Ser Leu Gln Ser Ser Asn Ile Glu Ser Lys Glu
535                 540                 545                 550 atc aat gga att cat gat gaa agc aat gct ttt gaa tca aaa gca tct      2395
Ile Asn Gly Ile His Asp Glu Ser Asn Ala Phe Glu Ser Lys Ala Ser
                555                 560                 565 gaa tcc att tct ttg aaa aac tta aaa agg cga tca caa ttt ttt gaa      2443
Glu Ser Ile Ser Leu Lys Asn Leu Lys Arg Arg Ser Gln Phe Phe Glu
            570                 575                 580 caa gga agc tct gat tcg gtg gtt cct gat ctt cca gtt cca acc atc      2491
Gln Gly Ser Ser Asp Ser Val Val Pro Asp Leu Pro Val Pro Thr Ile
    585                 590                 595 agt gcc ccg agt cgc tgg gtg tgg gat caa gag gag gag cgg aag cgg      2539
Ser Ala Pro Ser Arg Trp Val Trp Asp Gln Glu Glu Glu Arg Lys Arg
600                 605                 610 cag gag agg tgg cag aag gag cag gac cgc cta ctg cag gaa aaa tat      2587
Gln Glu Arg Trp Gln Lys Glu Gln Asp Arg Leu Leu Gln Glu Lys Tyr
615                 620                 625                 630 caa cgt gag cag gag aaa ctg agg gaa gag tgg caa agg gcc aaa cag      2635
Gln Arg Glu Gln Glu Lys Leu Arg Glu Glu Trp Gln Arg Ala Lys Gln
                635                 640                 645 gag gca gag aga gag aat tcc aag tac ttg gat gag gaa ctg atg gtc      2683
Glu Ala Glu Arg Glu Asn Ser Lys Tyr Leu Asp Glu Glu Leu Met Val
            650                 655                 660 cta agc tca aac agc atg tct ctg acc aca cgg gag ccc tct ctt gcc      2731
Leu Ser Ser Asn Ser Met Ser Leu Thr Thr Arg Glu Pro Ser Leu Ala
    665                 670                 675 acc tgg gaa gct acc tgg agt gaa ggg tcc aag tct tca gac aga gaa      2779
Thr Trp Glu Ala Thr Trp Ser Glu Gly Ser Lys Ser Ser Asp Arg Glu
680                 685                 690 gga acc cga gca gga gaa gag gag agg aga cag cca caa gag gaa gtt      2827
Gly Thr Arg Ala Gly Glu Glu Glu Arg Arg Gln Pro Gln Glu Glu Val
695                 700                 705                 710 gtt cat gag gac caa gga aag aag ccg cag gat cag ctt gtt att gag      2875
Val His Glu Asp Gln Gly Lys Lys Pro Gln Asp Gln Leu Val Ile Glu
                715                 720                 725 aga gag agg aaa tgg gag caa cag ctt cag gaa gag caa gag caa aag      2923
Arg Glu Arg Lys Trp Glu Gln Gln Leu Gln Glu Glu Gln Glu Gln Lys
            730                 735                 740 cgg ctt cag gct gag gct gag gag cag aag cgt cct gcg gag gag cag      2971
Arg Leu Gln Ala Glu Ala Glu Glu Gln Lys Arg Pro Ala Glu Glu Gln
    745                 750                 755 aag cgc cag gca gag ata gag cgg gaa aca tca gtc aga ata tac cag      3019
Lys Arg Gln Ala Glu Ile Glu Arg Glu Thr Ser Val Arg Ile Tyr Gln
760                 765                 770 tac agg agg cct gtt gat tcc tat gat ata cca aag aca gaa gaa gca      3067
Tyr Arg Arg Pro Val Asp Ser Tyr Asp Ile Pro Lys Thr Glu Glu Ala
775                 780                 785                 790 tct tca ggt ttt ctt cct ggt gac agg aat aaa tcc aga tct act act      3115
Ser Ser Gly Phe Leu Pro Gly Asp Arg Asn Lys Ser Arg Ser Thr Thr
                795                 800                 805
```

| | |
|---|---|
| gaa ctg gat gat tac tcc aca aat aaa aat gga aac aat aaa tat tta<br>Glu Leu Asp Asp Tyr Ser Thr Asn Lys Asn Gly Asn Asn Lys Tyr Leu<br>       810                 815                820 | 3163 |
| gac caa att ggg aac acg acc tct tca cag agg aga tcc aag aaa gaa<br>Asp Gln Ile Gly Asn Thr Thr Ser Ser Gln Arg Arg Ser Lys Lys Glu<br>       825                 830                835 | 3211 |
| caa gta cca tca gga gca gaa ttg gag agg caa caa atc ctt cag gaa<br>Gln Val Pro Ser Gly Ala Glu Leu Glu Arg Gln Gln Ile Leu Gln Glu<br>840                   845                850 | 3259 |
| atg agg aag aga aca ccc ctt cac aat gac aac agc tgg atc cga cag<br>Met Arg Lys Arg Thr Pro Leu His Asn Asp Asn Ser Trp Ile Arg Gln<br>855                   860                865                870 | 3307 |
| cgc agt gcc agt gtc aac aaa gag cct gtt agt ctt cct ggg atc atg<br>Arg Ser Ala Ser Val Asn Lys Glu Pro Val Ser Leu Pro Gly Ile Met<br>                 875                880                885 | 3355 |
| aga aga ggc gaa tct tta gat aac ctg gac tcc ccc gga tcc aat tct<br>Arg Arg Gly Glu Ser Leu Asp Asn Leu Asp Ser Pro Arg Ser Asn Ser<br>890                   895                900 | 3403 |
| tgg aga cag cct cct tgg ctc aat cag ccc aca gga ttc tat gct tct<br>Trp Arg Gln Pro Pro Trp Leu Asn Gln Pro Thr Gly Phe Tyr Ala Ser<br>       905                 910                915 | 3451 |
| tcc tct gtg caa gac ttt agt cgc cca cca cct cag ctg gtg tcc aca<br>Ser Ser Val Gln Asp Phe Ser Arg Pro Pro Pro Gln Leu Val Ser Thr<br>920                   925                930 | 3499 |
| tca aac cgt gcc tac atg cgg aac ccc tcc tcc agc gtg ccc cca cct<br>Ser Asn Arg Ala Tyr Met Arg Asn Pro Ser Ser Ser Val Pro Pro Pro<br>935                   940                945                950 | 3547 |
| tca gct ggc tcc gtg aag acc tcc acc aca ggt gtg gcc acc aca cag<br>Ser Ala Gly Ser Val Lys Thr Ser Thr Thr Gly Val Ala Thr Thr Gln<br>                 955                960                965 | 3595 |
| tcc ccc acc ccg aga agc cat tcc cct tca gct tca cag tca ggc tct<br>Ser Pro Thr Pro Arg Ser His Ser Pro Ser Ala Ser Gln Ser Gly Ser<br>970                   975                980 | 3643 |
| cag ctg cgt aac agg tca gtc agt ggg aag cgc ata tgc tcc tac tgc<br>Gln Leu Arg Asn Arg Ser Val Ser Gly Lys Arg Ile Cys Ser Tyr Cys<br>       985                 990                995 | 3691 |
| aat aac att ctg ggc aaa gga gcc gcc atg atc atc gag tcc ctg ggt<br>Asn Asn Ile Leu Gly Lys Gly Ala Ala Met Ile Ile Glu Ser Leu Gly<br>1000                1005              1010 | 3739 |
| ctt tgt tat cat ttg cat tgt ttt aag tgt gtt gcc tgt gag tgt gac<br>Leu Cys Tyr His Leu His Cys Phe Lys Cys Val Ala Cys Glu Cys Asp<br>1015                1020              1025              1030 | 3787 |
| ctc gga ggc tct tcc tca gga gct gaa gtc agg atc aga aac cac caa<br>Leu Gly Gly Ser Ser Ser Gly Ala Glu Val Arg Ile Arg Asn His Gln<br>                  1035              1040              1045 | 3835 |
| ctg tac tgc aac gac tgc tat ctc aga ttc aaa tct gga cgg cca acc<br>Leu Tyr Cys Asn Asp Cys Tyr Leu Arg Phe Lys Ser Gly Arg Pro Thr<br>1050                1055              1060 | 3883 |
| gcc atg tga tgtaagcctc catacgaaag cactgttgca gatagaagaa<br>Ala Met  * | 3932 |
| gaggtggttg ctgctcatgt agatctataa atatgtgttg tatgtctttt ttgcttttt | 3992 |
| tttaaaaaaa agaataactt tttttgcctc tttagattac atagaagcat tgtagtcttg | 4052 |
| gtagaaccag tattttttgtt gtttatttat aaggtaattg tgtgtgggga aaagtgcagt | 4112 |
| atttacctgt tgaattcagc atcttgagag cacaagggaa aaaataagaa cctacgaata | 4172 |
| ttttttgaggc agataatgat ctagtttgac tttctagtta gtggtgtttt gaagagggta | 4232 |
| ttttattgtt ttttaaaaaa aggttcttaa acattatttg aaatagttaa tataaataca | 4292 |

```
taattgcatt tgctctgttt attgtaatgt attctaaatt aatgcagaac catatggaaa   4352
atttcattaa aatctatccc caaatgtgct ttctgtatcc ttccttctac ctattattct   4412
gatttttaaa aatgcagtta atgtaccatt tatttgcttg atgaagggag ctctatttc   4472 tttaccagaa atgttgctaa gtaattccca atagaaagct gcttattttc attaatgaaa   4532
aataaccatg gtttgtatac tagaagtctt cttcagaaac tggtgagcct ttctgttcaa   4592
ttgcatttgt aaataaactt gctgatgcat ttaaaaaaaa aaaaaaaaaa               4642
```

<210> SEQ ID NO 4
<211> LENGTH: 1064
<212> TYPE: PRT
<213> ORGANISM: Homo Sapiens

<400> SEQUENCE: 4

```
Met Gln Asp Tyr Asn Lys Asp Asp Met Ser Tyr Arg Arg Ile Ser Ala
 1               5                  10                  15

Val Glu Pro Lys Thr Ala Leu Pro Phe Asn Arg Phe Leu Pro Asn Lys
            20                  25                  30

Ser Arg Gln Pro Ser Tyr Val Pro Ala Pro Leu Arg Lys Lys Lys Pro
        35                  40                  45

Asp Lys His Glu Asp Asn Arg Arg Ser Trp Ala Ser Pro Val Tyr Thr
    50                  55                  60

Glu Ala Asp Gly Thr Phe Ser Arg Leu Phe Gln Lys Ile Tyr Gly Glu
65                  70                  75                  80

Asn Gly Ser Lys Ser Met Ser Asp Val Ser Ala Glu Asp Val Gln Asn
                85                  90                  95

Leu Arg Gln Leu Arg Tyr Glu Glu Met Gln Lys Ile Lys Ser Gln Leu
            100                 105                 110

Lys Glu Gln Asp Gln Lys Trp Gln Asp Asp Leu Ala Lys Trp Lys Asp
        115                 120                 125

Arg Arg Lys Ser Tyr Thr Ser Asp Leu Gln Lys Lys Glu Glu Arg
    130                 135                 140

Glu Glu Ile Glu Lys Gln Ala Leu Glu Lys Ser Lys Arg Ser Ser Lys
145                 150                 155                 160

Thr Phe Lys Glu Met Leu Gln Asp Arg Glu Ser Gln Asn Gln Lys Ser
                165                 170                 175

Thr Val Pro Ser Arg Arg Met Tyr Ser Phe Asp Asp Val Leu Glu
            180                 185                 190

Glu Gly Lys Arg Pro Pro Thr Met Thr Val Ser Glu Ala Ser Tyr Gln
        195                 200                 205

Ser Glu Arg Val Glu Glu Lys Gly Ala Thr Tyr Pro Ser Glu Ile Pro
    210                 215                 220

Lys Glu Asp Ser Thr Thr Phe Ala Lys Arg Glu Asp Arg Val Thr Thr
225                 230                 235                 240

Glu Ile Gln Leu Pro Ser Gln Ser Pro Val Glu Glu Gln Ser Pro Ala
                245                 250                 255

Ser Leu Ser Ser Leu Arg Ser Arg Ser Thr Gln Met Glu Ser Thr Arg
            260                 265                 270

Val Ser Ala Ser Leu Pro Arg Ser Tyr Arg Lys Thr Asp Thr Val Arg
        275                 280                 285

Leu Thr Ser Val Val Thr Pro Arg Pro Phe Gly Ser Gln Thr Arg Gly
    290                 295                 300

Ile Ser Ser Leu Pro Arg Ser Tyr Thr Met Asp Asp Ala Trp Lys Tyr
305                 310                 315                 320
```

```
Asn Gly Asp Val Glu Asp Ile Lys Arg Thr Pro Asn Asn Val Val Ser
            325                 330                 335

Thr Pro Ala Pro Ser Pro Asp Ala Ser Gln Leu Ala Ser Ser Leu Ser
            340                 345                 350

Ser Gln Lys Glu Val Ala Ala Thr Glu Glu Asp Val Thr Arg Leu Pro
            355                 360                 365

Ser Pro Thr Ser Pro Phe Ser Ser Leu Ser Gln Asp Gln Ala Ala Thr
            370                 375                 380

Ser Lys Ala Thr Leu Ser Ser Thr Ser Gly Leu Asp Leu Met Ser Glu
385                 390                 395                 400

Ser Gly Glu Gly Glu Ile Ser Pro Gln Arg Glu Val Ser Arg Ser Gln
            405                 410                 415

Asp Gln Phe Ser Asp Met Arg Ile Ser Ile Asn Gln Thr Pro Gly Lys
            420                 425                 430

Ser Leu Asp Phe Gly Phe Thr Ile Lys Trp Asp Ile Pro Gly Ile Phe
            435                 440                 445

Val Ala Ser Val Glu Ala Gly Ser Pro Ala Glu Phe Ser Gln Leu Gln
            450                 455                 460

Val Asp Asp Glu Ile Ile Ala Ile Asn Asn Thr Lys Phe Ser Tyr Asn
465                 470                 475                 480

Asp Ser Lys Glu Trp Glu Ala Met Ala Lys Ala Gln Glu Thr Gly
            485                 490                 495

His Leu Val Met Asp Val Arg Arg Tyr Gly Lys Ala Gly Ser Pro Glu
            500                 505                 510

Thr Lys Trp Ile Asp Ala Thr Ser Gly Ile Tyr Asn Ser Glu Lys Ser
            515                 520                 525

Ser Asn Leu Ser Val Thr Thr Asp Phe Ser Glu Ser Leu Gln Ser Ser
530                 535                 540

Asn Ile Glu Ser Lys Glu Ile Asn Gly Ile His Asp Glu Ser Asn Ala
545                 550                 555                 560

Phe Glu Ser Lys Ala Ser Glu Ser Ile Ser Leu Lys Asn Leu Lys Arg
            565                 570                 575

Arg Ser Gln Phe Phe Glu Gln Gly Ser Ser Asp Ser Val Val Pro Asp
            580                 585                 590

Leu Pro Val Pro Thr Ile Ser Ala Pro Ser Arg Trp Val Trp Asp Gln
            595                 600                 605

Glu Glu Glu Arg Lys Arg Gln Glu Arg Trp Gln Lys Glu Gln Asp Arg
            610                 615                 620

Leu Leu Gln Glu Lys Tyr Gln Arg Glu Gln Lys Leu Arg Glu Glu
625                 630                 635                 640

Trp Gln Arg Ala Lys Gln Glu Ala Glu Arg Glu Asn Ser Lys Tyr Leu
            645                 650                 655

Asp Glu Glu Leu Met Val Leu Ser Ser Asn Ser Met Ser Leu Thr Thr
            660                 665                 670

Arg Glu Pro Ser Leu Ala Thr Trp Glu Ala Thr Trp Ser Glu Gly Ser
            675                 680                 685

Lys Ser Ser Asp Arg Glu Gly Thr Arg Ala Gly Glu Glu Arg Arg
            690                 695                 700

Gln Pro Gln Glu Glu Val Val His Glu Asp Gln Gly Lys Lys Pro Gln
705                 710                 715                 720

Asp Gln Leu Val Ile Glu Arg Glu Arg Lys Trp Glu Gln Gln Leu Gln
            725                 730                 735
```

```
Glu Glu Gln Glu Gln Lys Arg Leu Gln Ala Glu Ala Glu Gln Lys
            740                 745                 750
Arg Pro Ala Glu Glu Lys Arg Gln Ala Glu Ile Glu Arg Glu Thr
            755                 760                 765
Ser Val Arg Ile Tyr Gln Tyr Arg Arg Pro Val Asp Ser Tyr Asp Ile
            770                 775                 780
Pro Lys Thr Glu Glu Ala Ser Ser Gly Phe Leu Pro Gly Asp Arg Asn
785                 790                 795                 800
Lys Ser Arg Ser Thr Thr Glu Leu Asp Asp Tyr Ser Thr Asn Lys Asn
                805                 810                 815
Gly Asn Asn Lys Tyr Leu Asp Gln Ile Gly Asn Thr Thr Ser Ser Gln
                820                 825                 830
Arg Arg Ser Lys Lys Glu Gln Val Pro Ser Gly Ala Glu Leu Glu Arg
                835                 840                 845
Gln Gln Ile Leu Gln Glu Met Arg Lys Arg Thr Pro Leu His Asn Asp
                850                 855                 860
Asn Ser Trp Ile Arg Gln Arg Ser Ala Ser Val Asn Lys Glu Pro Val
865                 870                 875                 880
Ser Leu Pro Gly Ile Met Arg Arg Gly Glu Ser Leu Asp Asn Leu Asp
                885                 890                 895
Ser Pro Arg Ser Asn Ser Trp Arg Gln Pro Pro Trp Leu Asn Gln Pro
                900                 905                 910
Thr Gly Phe Tyr Ala Ser Ser Val Gln Asp Phe Ser Arg Pro Pro
                915                 920                 925
Pro Gln Leu Val Ser Thr Ser Asn Arg Ala Tyr Met Arg Asn Pro Ser
                930                 935                 940
Ser Ser Val Pro Pro Ser Ala Gly Ser Val Lys Thr Ser Thr Thr
945                 950                 955                 960
Gly Val Ala Thr Thr Gln Ser Pro Thr Pro Arg Ser His Ser Pro Ser
                965                 970                 975
Ala Ser Gln Ser Gly Ser Gln Leu Arg Asn Arg Ser Val Ser Gly Lys
                980                 985                 990
Arg Ile Cys Ser Tyr Cys Asn Asn Ile Leu Gly Lys Gly Ala Ala Met
                995                 1000                1005
Ile Ile Glu Ser Leu Gly Leu Cys Tyr His Leu His Cys Phe Lys Cys
            1010                1015                1020
Val Ala Cys Glu Cys Asp Leu Gly Gly Ser Ser Gly Ala Glu Val
1025                1030                1035                1040
Arg Ile Arg Asn His Gln Leu Tyr Cys Asn Asp Cys Tyr Leu Arg Phe
                1045                1050                1055
Lys Ser Gly Arg Pro Thr Ala Met
            1060

<210> SEQ ID NO 5
<211> LENGTH: 549
<212> TYPE: DNA
<213> ORGANISM: Homo Sapiens

<400> SEQUENCE: 5
gcaccataag agagaagatt cctttgaaag cttggactct tgggctcga ggtcattgac      60 aagctgctcc tctgatatca cgttgagagg ggggcgtgaa ggttttgaaa gtgacacaga    120
ttcggaattt acattcaaga tgcaggatta taataaagat gatatgtcgt atcgaaggat    180
ttcggctgtt gagccaaaga ctgcgttacc cttcaatcgt tttttaccca acaaaagtag    240
```

-continued

| | |
|---|---|
| acagccatcc tatgtaccag cacctctgag aaagaaaaag ccagacaaac atgaggataa | 300 |
| cagaagaagt tgggcaagcc cggtttatac agaagcagat ggaacatttt caagactctt | 360 |
| tcaaaagatt tatggtgaga atgggagtaa gtccatgagt gatgtcagcg cagaagatgt | 420 |
| tcaaaacttg cgtcagctgc gttacgagga gatgcagaaa ataaaatcac aattaaaaga | 480 |
| acaagatcag aaatggcagg atgaccttgc aaagtggaaa gatcgtcgaa aaagttacac | 540 |
| ttcagatct | 549 |

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6

| | |
|---|---|
| gtaactttttt cgacgatctt tccac | 25 |

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7

| | |
|---|---|
| tattttctgc atctcctcgt aacgc | 25 |

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8

| | |
|---|---|
| tgacatcact catggactta ctccc | 25 |

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9

| | |
|---|---|
| gttccatctg cttctgtata aaccg | 25 |

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10

| | |
|---|---|
| tctgttatcc tcatgtttgt ctggc | 25 |

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
tctggctttt tctttctcaa agtgc                        25

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
aagtgctggt acatagatgg ctgtc                        25

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
tctacttttg ttggggttga aaacg                        25

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
tgtgtcactt tcaaaaactt cacgc                        25

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
agagcagctt gtctatgaac tccag                        25

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
cgggaaatcg tgcgtgacat taag                        24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
tgatctcctt ctgcatcctg tcgg                        24

<210> SEQ ID NO 18

```
<211> LENGTH: 23
<212> TYPE: DNA
<213> ORGANISM: Artificial Sequence
<220> FEATURE:
<223> OTHER INFORMATION: Primer

<400> SEQUENCE: 18
ttcgtagcat cagttgaagc agg                                            23

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
ggtgaaccag cctttccata gc                                             22
```